(12) United States Patent
Miyazono et al.

(10) Patent No.: US 6,194,187 B1
(45) Date of Patent: Feb. 27, 2001

(54) APOPTOSIS-INDUCING PROTEIN AND GENE ENCODING THE SAME

(75) Inventors: Kohei Miyazono, Shiki; Hidenori Ichijo, Bunkyo-ku, both of (JP)

(73) Assignee: Japanese Foundation for Cancer Research, Tokyo-to (JP)

( * ) Notice: Subject to any disclaimer, the term of this patent is extended or adjusted under 35 U.S.C. 154(b) by 0 days.

(21) Appl. No.: 09/171,410

(22) PCT Filed: Apr. 18, 1997

(86) PCT No.: PCT/JP97/01348

§ 371 Date: Dec. 4, 1998

§ 102(e) Date: Dec. 4, 1998

(87) PCT Pub. No.: WO97/40143

PCT Pub. Date: Oct. 30, 1997

(30) Foreign Application Priority Data

Apr. 19, 1996 (JP) .................................................. 8-122320
Aug. 23, 1996 (JP) .................................................. 8-241063

(51) Int. Cl.[7] .............................. C12N 9/12; C12N 1/20; C12N 15/00; A61K 38/51; C07H 21/04

(52) U.S. Cl. ...................... 435/194; 435/320.1; 435/325; 435/252.3; 435/254.2; 435/348; 435/365; 435/357; 435/358; 435/352; 424/94.5; 536/23.2; 514/44

(58) Field of Search ................................ 435/194, 320.1, 435/252.3, 325, 252.33, 248, 365, 352, 357, 358; 536/23.2; 514/44; 530/387.9; 424/94.5

(56) References Cited

PUBLICATIONS

Genbank–est111 Database, accession No. T78387, Mar. 1995.*
Tibbles et al., EMBO J., 15(24), 7026–7035, Aug. 1996.*
Rana et al., J.B.C., 271(32), 19025–19028, Aug. 1996.*
Wang et al., "Molecular Cloning and Characterization of a Novel Protien Kinase with a Catalytic Domain Homologous to Mitogen–activated Protein Kinase Kinase*", The Journal of Biological Chemistry, vol. 271, No. 49, pp. 31607–31611, Dec. 6, 1996.
Hidenori Ichijo et al., "Induction of Apoptosis by Ask1, a Mammalian MAPKKK that Activates SAPK/JNK and p38 Signaling Pathways", This week In Science, vol. 275, Jan. 3, 1997, pp. 90–94.
Blank et al., "Molecular Cloning of Mitogen–activated Protien/ERK Kinases (MEKK) 2 and 3", The Journal of Biological Chemistry, vol. 271, No. 10, pp. 5361–5368, Mar. 8, 1996.

* cited by examiner

Primary Examiner—Rebecca E. Prouty
Assistant Examiner—Maryam Monshipouri
(74) Attorney, Agent, or Firm—Foley & Lardner

(57) ABSTRACT

An object of the present invention is to provide a protein which induces apoptosis, a base sequence encoding the protein, and an agent for use in the treatment of malignant tumors. The present invention is a protein (ASK1) which has protein kinase activity and enhances SEK1 kinase activity and/or MKK3 kinase activity, or a derivative thereof. Malignant tumors can be treated using the protein according to the present invention or the base sequence encoding the protein.

25 Claims, 16 Drawing Sheets

MSTEADEGITFSVPPFAPSGFCTIPEGGICRRGGAAAVGEGEEHQLPPPPPGSFWNVESA 60
→ clone 20
AAPGIGCPAATSSSSATRGRGSSVGGGSRRTTVAYVINEASQGQLVVAESEALQSLREAC 120
ETVGATLETLHFGKLDFGETTVLDRFYNADIAVVEMSDAFRQPSLFYHLGVRESFSMANN 180
IILYCDTNSDSLQSLKEIICQKNTMCTGNYTFVPYMITPHNKVYCCDSSFMKGLTELMQP 240
NFELLLGPICLPLVDRFIQLLKVAQASSSQYFRESILNDIRKARNLYTGKELAAELARIR 300
QRVDNIEVLTADIVINLLLSYRDIQDYDSIVKLVETLEKLPTFDLASHHHVKFHYAFALN 360
RRNLPGDRAKALDIMIPMVQSEGQVASDMYCLVGRIYKDMFLDSNFTDTESRDHGASWFK 420
→ clone 27
KAFESEPTLQSGINYAVLLLAAGHQFESSFELRKVGVKLSSLLGKKGNLEKLQSYWEVGF 480
FLGASVLANDHMRVIQASEKLFKLKTPAWYLKSIVETILIYKHFVKLTTEQPVAKQELVD 540
FWMDFLVEATKTDVTVVRFPVLILEPTKIYQPSYLSINNEVEEKTISIWHVLPDDKKGIH 600
EWNFSASSVRGVSISKFEERCCFLYVLHNSDDFQIYFCTELHCKKFFEMVNTITEEKGRS 660
TEEGDCESDLLEYDYEYDENGDRVVLGKGTYGIVYAGRDLSNQVRIAIKEIPERDSRYSQ 720
PLHEEIALHKHLKHKNIVQYLGSFSENGFIKIFMEQVPGGSLYALLRSKWGPLKDNEQTI 780
GFYTKQILEGLKYLHDNQIVHRDIKGDNVLINTYSGVLKISDFGTSKRLAGINPCTETFT 840
GTLQYMAPEIIDKGPRGYGKAADIWSLGCTIIEMATGKPPFYELGEPQAAMFKVGMFKVH 900
PEIPESMSAEAKAFILKCFEPDPDKRACANDLLVDEFLKVSSKKKKTQPKLSALSAGSNA 960
EYLRSISLPVPVLVEDTSSSSEYGSVSPDTELKVDPFSFKTRAKSCGERDVKGIRTLFLG 1020
IPDENFEDHSAPPSPEEKDSGFFMLRKDSERRATLHRILTEDQDKIVRNLMESLAQGAEE 1080
PKLKWEHITTLIASLREFVRSTDRKIIATTLSKLKLELDFDSHGISQVQVVLFGFQDAVN 1140
KVLRNHNIKPHWMFALDSIIRKAVQTAITILVPELRPHFSLASESDTADQEDLDVEDDHE 1200
EQPSNQTVRRPQAVIEDAVATSGVSTLSSTVSHDSQSAHRSLNVQLGRMKIETNRLLEEL 1260
VRKEKELQALLHRAIEEKDQEIKHLKLKSQPIEIPELPVFHLNSSGTNIEDSELTDWLRV 1320
NGADEDTISRFLAEDYTLLDVLYYVTRDDLKCLRLRGGMLCTLWKAIIDFRNKQT 1375

FIG. 1

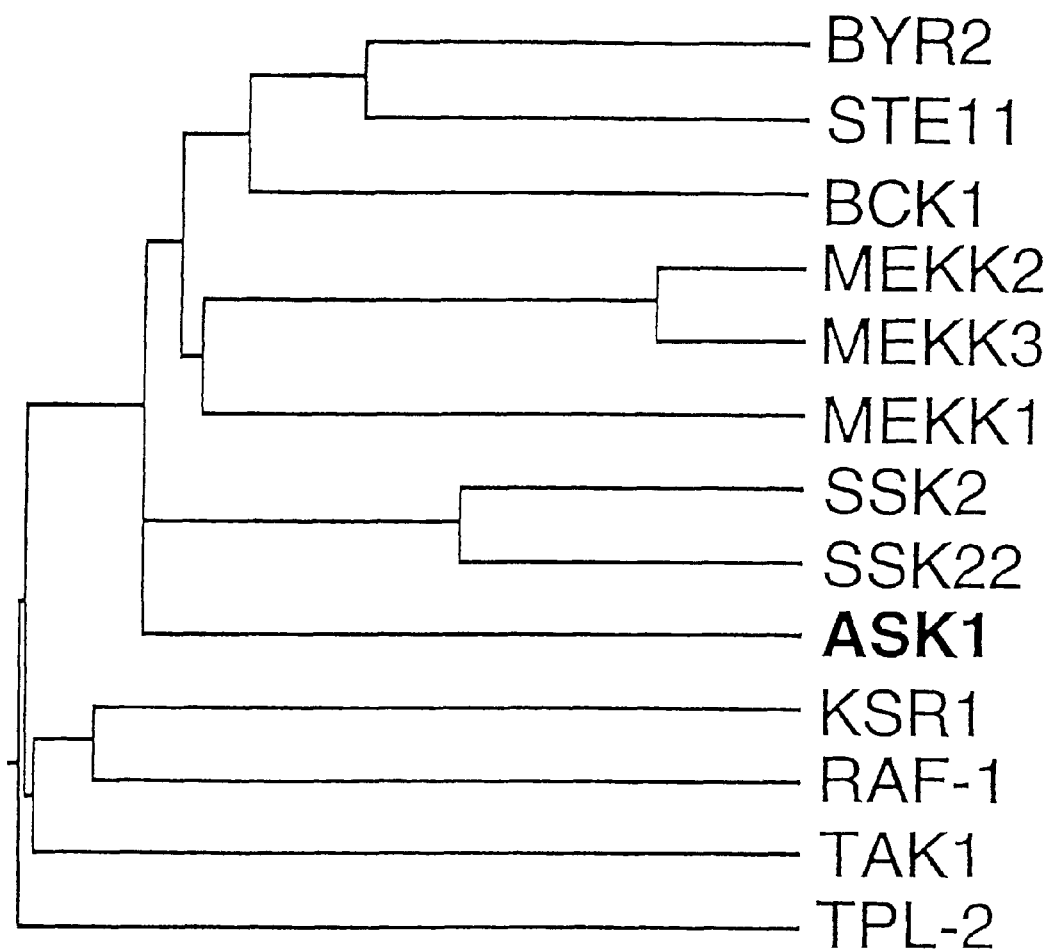
F I G. 2

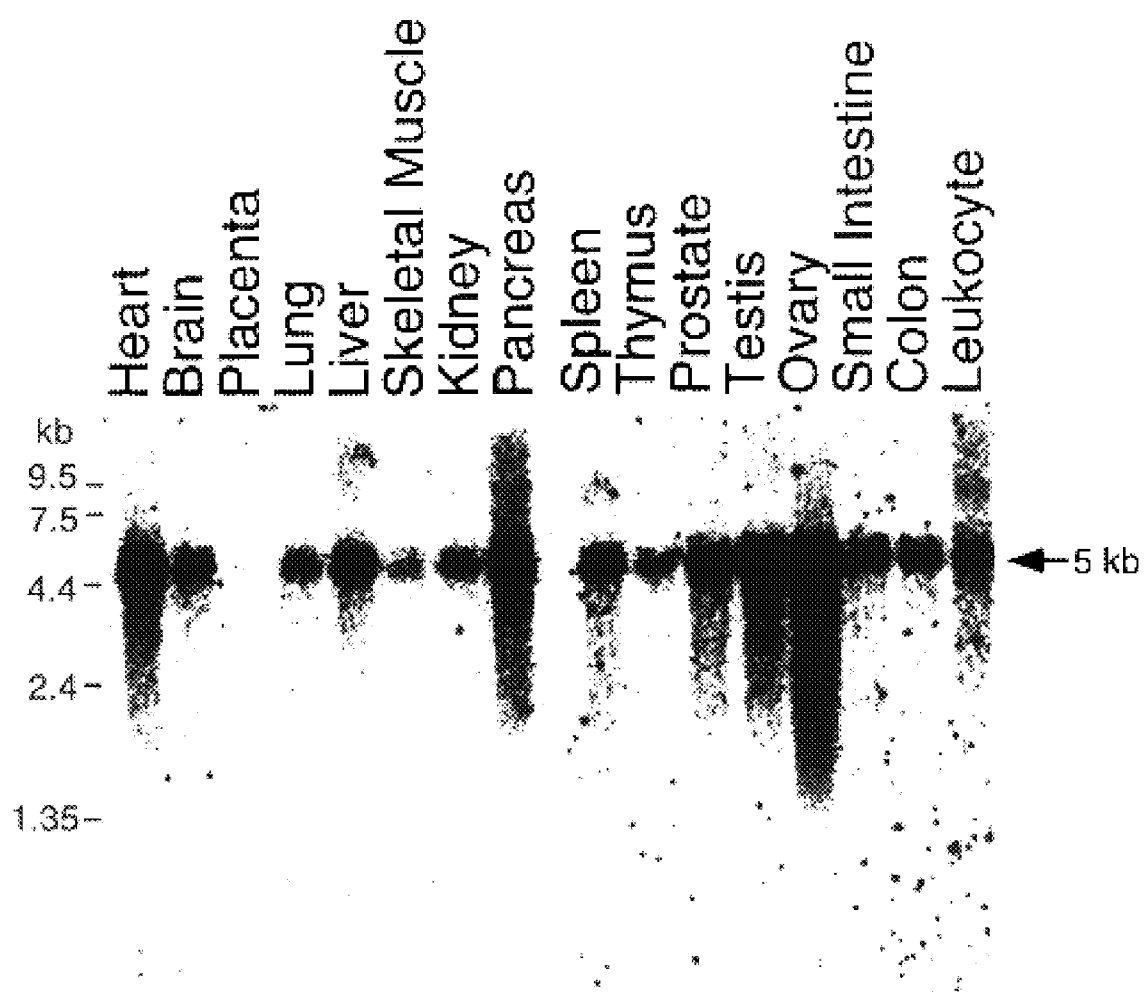
F I G. 3

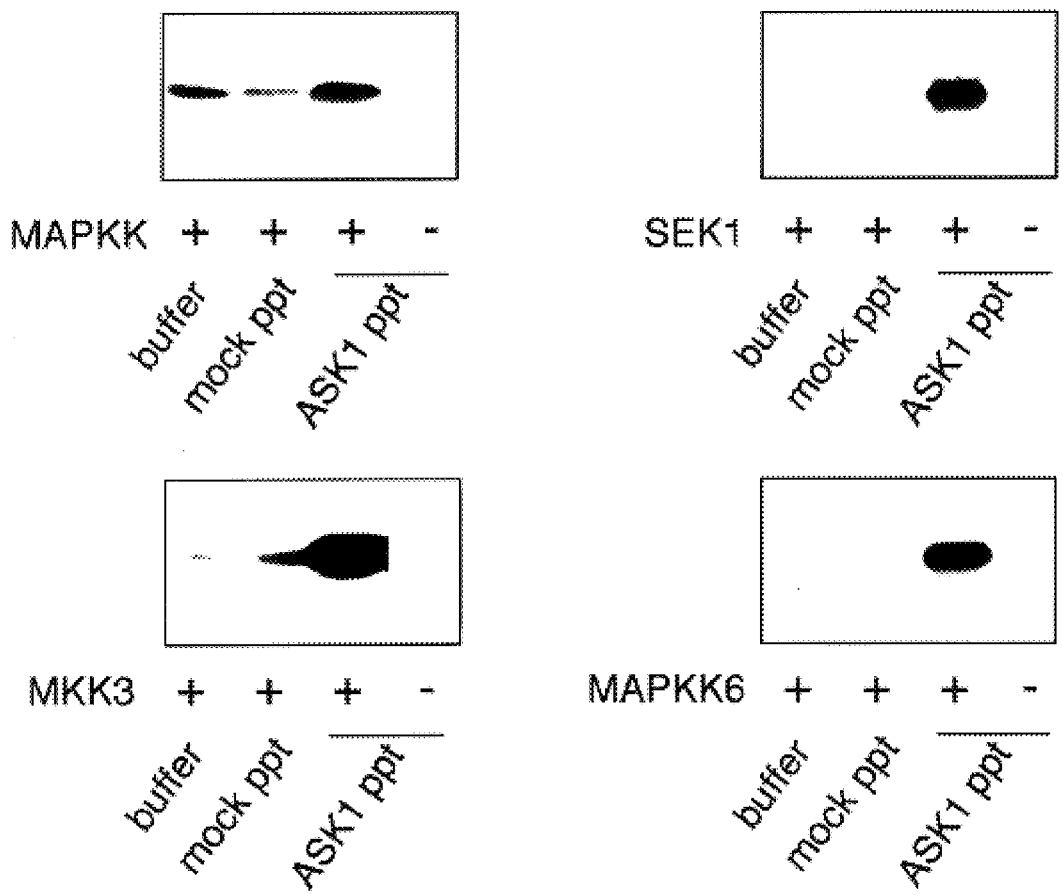
F I G. 6

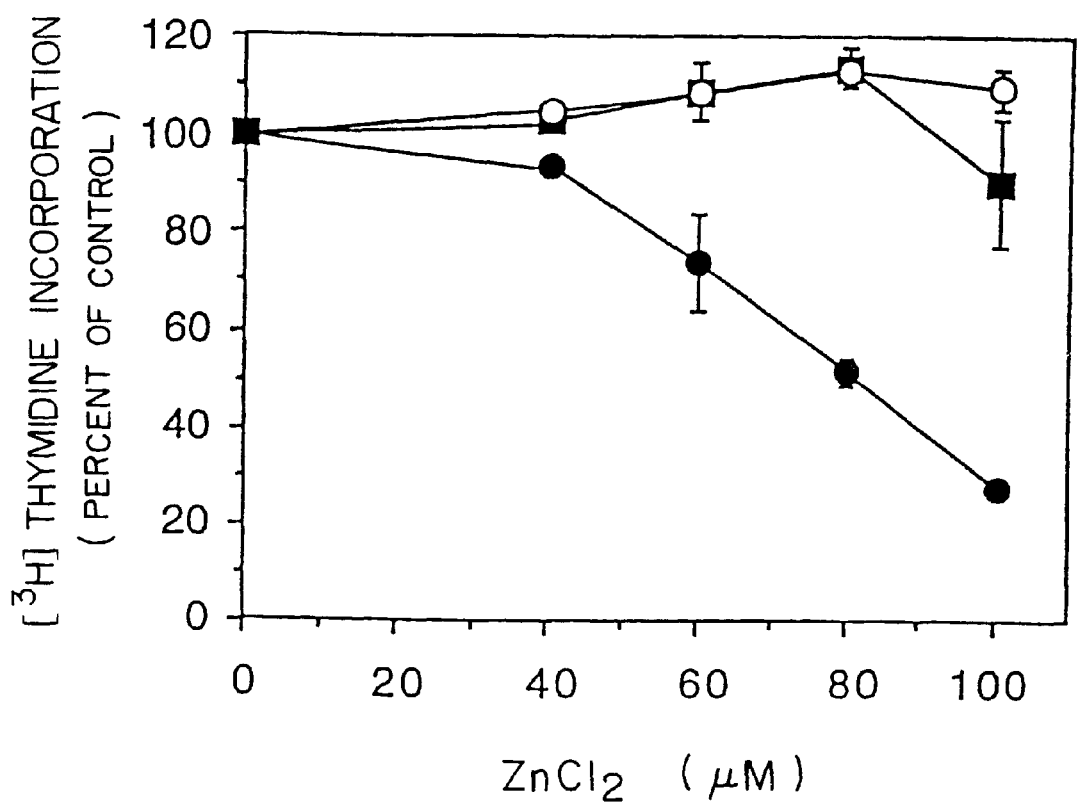
F I G. 8

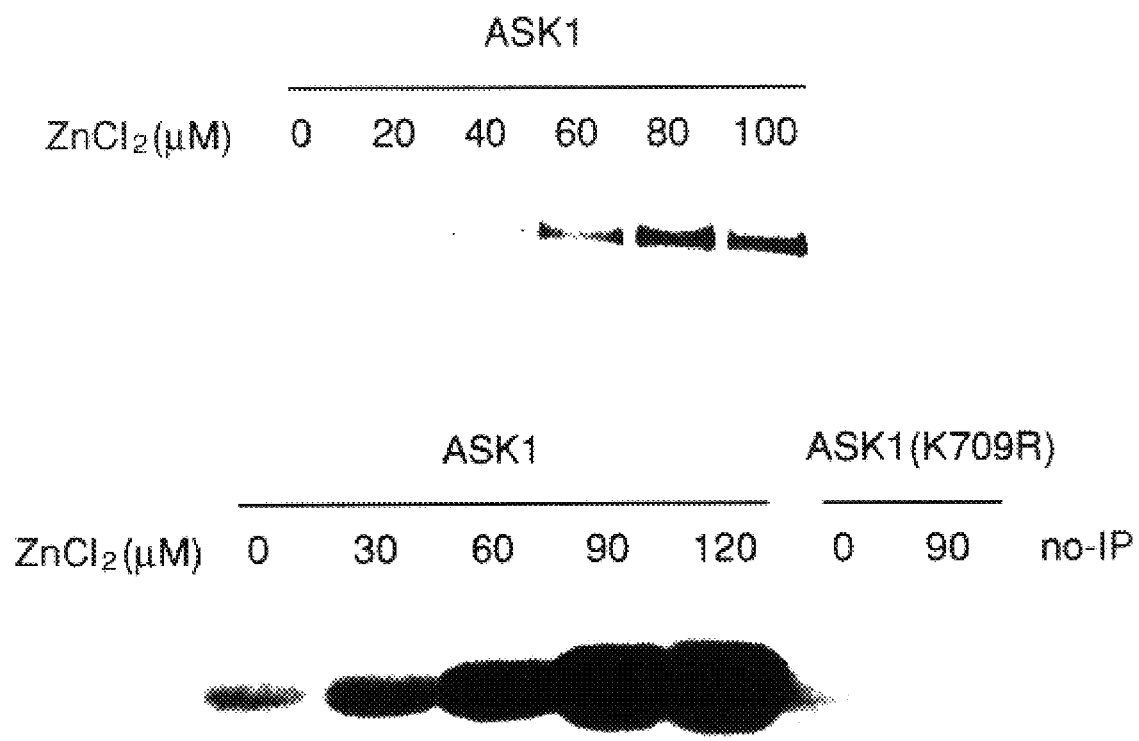
F I G. 9

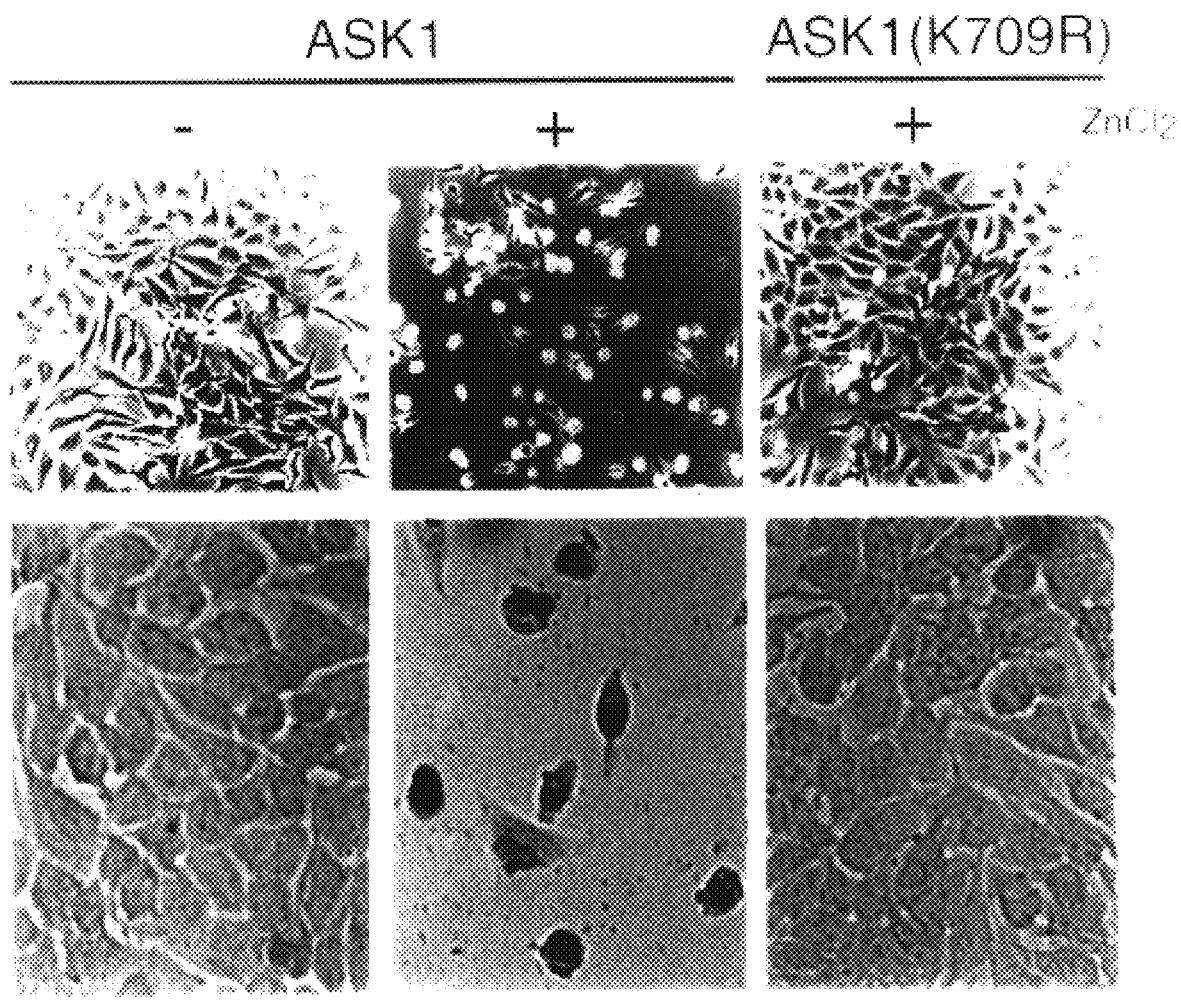
F I G. 11

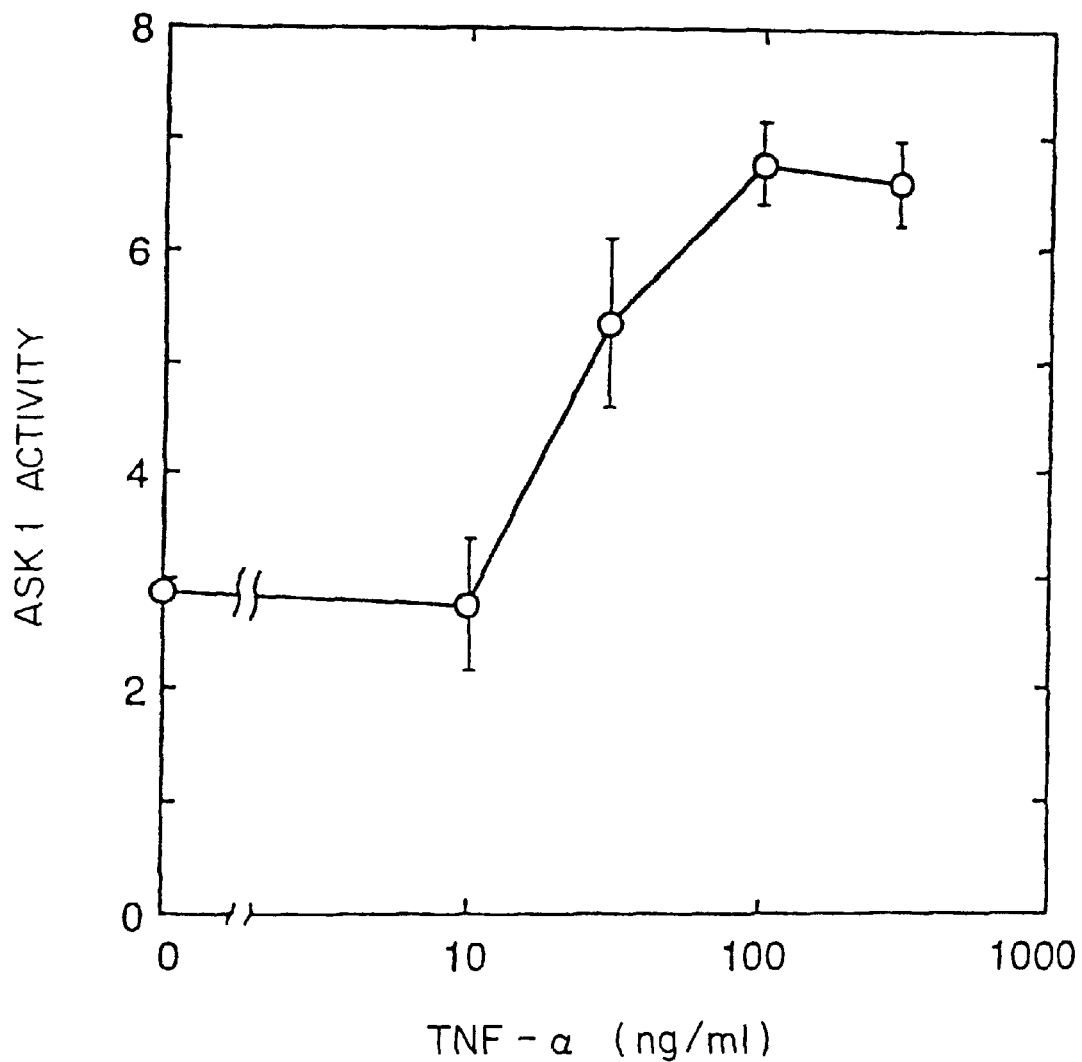
F I G. 14

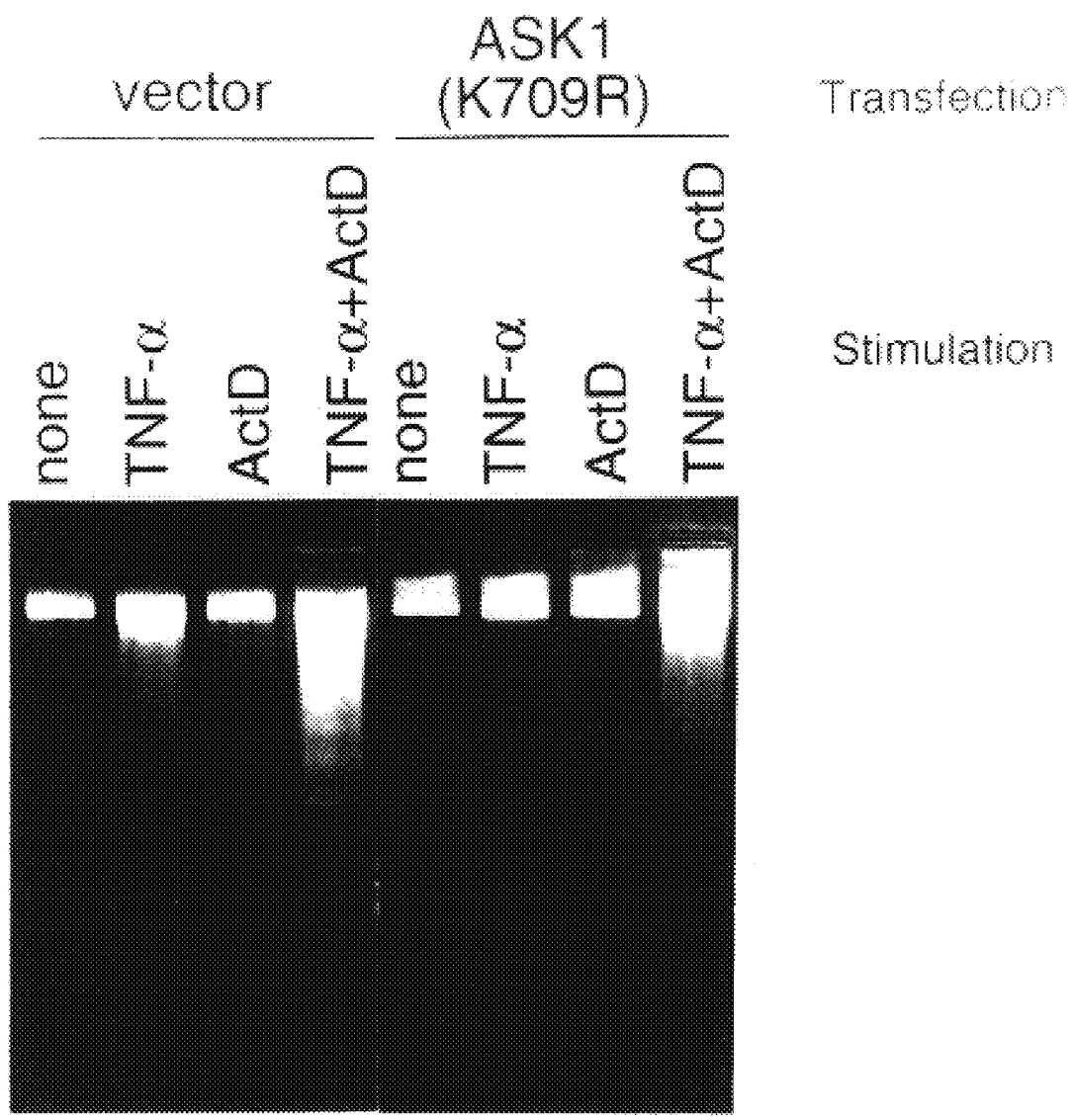
F I G. 15

SEQUENCE LISTING

<160> NUMBER OF SEQ ID NOS: 3

<210> SEQ ID NO 1
<211> LENGTH: 1375
<212> TYPE: PRT
<213> ORGANISM: Homo sapiens

<400> SEQUENCE: 1

-continued

```
Met Ser Thr Glu Ala Asp Glu Gly Ile Thr Phe Ser Val Pro Pro Phe
 1               5                  10                 15

Ala Pro Ser Gly Phe Cys Thr Ile Pro Glu Gly Gly Ile Cys Arg Arg
                20                  25                 30

Gly Gly Ala Ala Ala Val Gly Glu Gly Glu Glu His Gln Leu Pro Pro
                35                  40                 45

Pro Pro Pro Gly Ser Phe Trp Asn Val Glu Ser Ala Ala Ala Pro Gly
        50                  55                 60

Ile Gly Cys Pro Ala Ala Thr Ser Ser Ser Ala Thr Arg Gly Arg
65                  70                  75                 80

Gly Ser Ser Val Gly Gly Gly Ser Arg Arg Thr Thr Val Ala Tyr Val
                85                  90                 95

Ile Asn Glu Ala Ser Gln Gly Gln Leu Val Val Ala Glu Ser Glu Ala
                100                 105                110

Leu Gln Ser Leu Arg Glu Ala Cys Glu Thr Val Gly Ala Thr Leu Glu
                115                 120                125

Thr Leu His Phe Gly Lys Leu Asp Phe Gly Glu Thr Thr Val Leu Asp
        130                 135                140

Arg Phe Tyr Asn Ala Asp Ile Ala Val Val Glu Met Ser Asp Ala Phe
145                 150                 155                160

Arg Gln Pro Ser Leu Phe Tyr His Leu Gly Val Arg Glu Ser Phe Ser
                165                 170                175

Met Ala Asn Asn Ile Ile Leu Tyr Cys Asp Thr Asn Ser Asp Ser Leu
                180                 185                190

Gln Ser Leu Lys Glu Ile Ile Cys Gln Lys Asn Thr Met Cys Thr Gly
                195                 200                205

Asn Tyr Thr Phe Val Pro Tyr Met Ile Thr Pro His Asn Lys Val Tyr
        210                 215                220

Cys Cys Asp Ser Ser Phe Met Lys Gly Leu Thr Glu Leu Met Gln Pro
225                 230                 235                240

Asn Phe Glu Leu Leu Leu Gly Pro Ile Cys Leu Pro Leu Val Asp Arg
                245                 250                255

Phe Ile Gln Leu Leu Lys Val Ala Gln Ala Ser Ser Ser Gln Tyr Phe
                260                 265                270

Arg Glu Ser Ile Leu Asn Asp Ile Arg Lys Ala Arg Asn Leu Tyr Thr
        275                 280                 285

Gly Lys Glu Leu Ala Ala Glu Leu Ala Arg Ile Arg Gln Arg Val Asp
        290                 295                 300

Asn Ile Glu Val Leu Thr Ala Asp Ile Val Ile Asn Leu Leu Leu Ser
305                 310                 315                320

Tyr Arg Asp Ile Gln Asp Tyr Asp Ser Ile Val Lys Leu Val Glu Thr
                325                 330                335

Leu Glu Lys Leu Pro Thr Phe Asp Leu Ala Ser His His Val Lys
                340                 345                350

Phe His Tyr Ala Phe Ala Leu Asn Arg Arg Asn Leu Pro Gly Asp Arg
                355                 360                365

Ala Lys Ala Leu Asp Ile Met Ile Pro Met Val Gln Ser Glu Gly Gln
        370                 375                 380

Val Ala Ser Asp Met Tyr Cys Leu Val Gly Arg Ile Tyr Lys Asp Met
385                 390                 395                400

Phe Leu Asp Ser Asn Phe Thr Asp Thr Glu Ser Arg Asp His Gly Ala
                405                 410                415
```

```
Ser Trp Phe Lys Lys Ala Phe Glu Ser Glu Pro Thr Leu Gln Ser Gly
            420                 425                 430

Ile Asn Tyr Ala Val Leu Leu Ala Ala Gly His Gln Phe Glu Ser
        435                 440                 445

Ser Phe Glu Leu Arg Lys Val Gly Val Lys Leu Ser Ser Leu Leu Gly
    450                 455                 460

Lys Lys Gly Asn Leu Glu Lys Leu Gln Ser Tyr Trp Glu Val Gly Phe
465                 470                 475                 480

Phe Leu Gly Ala Ser Val Leu Ala Asn Asp His Met Arg Val Ile Gln
                485                 490                 495

Ala Ser Glu Lys Leu Phe Lys Leu Lys Thr Pro Ala Trp Tyr Leu Lys
            500                 505                 510

Ser Ile Val Glu Thr Ile Leu Ile Tyr Lys His Phe Val Lys Leu Thr
            515                 520                 525

Thr Glu Gln Pro Val Ala Lys Gln Glu Leu Val Asp Phe Trp Met Asp
            530                 535                 540

Phe Leu Val Glu Ala Thr Lys Thr Asp Val Thr Val Arg Phe Pro
545                 550                 555                 560

Val Leu Ile Leu Glu Pro Thr Lys Ile Tyr Gln Pro Ser Tyr Leu Ser
                565                 570                 575

Ile Asn Asn Glu Val Glu Glu Lys Thr Ile Ser Ile Trp His Val Leu
                580                 585                 590

Pro Asp Asp Lys Lys Gly Ile His Glu Trp Asn Phe Ser Ala Ser Ser
                595                 600                 605

Val Arg Gly Val Ser Ile Ser Lys Phe Glu Arg Cys Cys Phe Leu
    610                 615                 620

Tyr Val Leu His Asn Ser Asp Asp Phe Gln Ile Tyr Phe Cys Thr Glu
625                 630                 635                 640

Leu His Cys Lys Lys Phe Phe Glu Met Val Asn Thr Ile Thr Glu Glu
                645                 650                 655

Lys Gly Arg Ser Thr Glu Glu Gly Asp Cys Glu Ser Asp Leu Leu Glu
                660                 665                 670

Tyr Asp Tyr Glu Tyr Asp Glu Asn Gly Asp Arg Val Val Leu Gly Lys
            675                 680                 685

Gly Thr Tyr Gly Ile Val Tyr Ala Gly Arg Asp Leu Ser Asn Gln Val
    690                 695                 700

Arg Ile Ala Ile Lys Glu Ile Pro Glu Arg Asp Ser Arg Tyr Ser Gln
705                 710                 715                 720

Pro Leu His Glu Glu Ile Ala Leu His Lys His Leu Lys His Lys Asn
                725                 730                 735

Ile Val Gln Tyr Leu Gly Ser Phe Ser Glu Asn Gly Phe Ile Lys Ile
                740                 745                 750

Phe Met Glu Gln Val Pro Gly Gly Ser Leu Tyr Ala Leu Leu Arg Ser
            755                 760                 765

Lys Trp Gly Pro Leu Lys Asp Asn Glu Gln Thr Ile Gly Phe Tyr Thr
770                 775                 780

Lys Gln Ile Leu Glu Gly Leu Lys Tyr Leu His Asp Asn Gln Ile Val
785                 790                 795                 800

His Arg Asp Ile Lys Gly Asp Asn Val Leu Ile Asn Thr Tyr Ser Gly
                805                 810                 815

Val Leu Lys Ile Ser Asp Phe Gly Thr Ser Lys Arg Leu Ala Gly Ile
            820                 825                 830

Asn Pro Cys Thr Glu Thr Phe Thr Gly Thr Leu Gln Tyr Met Ala Pro
```

-continued

```
                835                 840                 845
Glu Ile Ile Asp Lys Gly Pro Arg Gly Tyr Gly Lys Ala Ala Asp Ile
            850                 855                 860
Trp Ser Leu Gly Cys Thr Ile Ile Glu Met Ala Thr Gly Lys Pro Pro
865                 870                 875                 880
Phe Tyr Glu Leu Gly Glu Pro Gln Ala Ala Met Phe Lys Val Gly Met
                885                 890                 895
Phe Lys Val His Pro Glu Ile Pro Glu Ser Met Ser Ala Glu Ala Lys
            900                 905                 910
Ala Phe Ile Leu Lys Cys Phe Glu Pro Asp Pro Asp Lys Arg Ala Cys
            915                 920                 925
Ala Asn Asp Leu Leu Val Asp Glu Phe Leu Lys Val Ser Ser Lys Lys
            930                 935                 940
Lys Lys Thr Gln Pro Lys Leu Ser Ala Leu Ser Ala Gly Ser Asn Ala
945                 950                 955                 960
Glu Tyr Leu Arg Ser Ile Ser Leu Pro Val Pro Val Leu Val Glu Asp
                965                 970                 975
Thr Ser Ser Ser Ser Glu Tyr Gly Ser Val Ser Pro Asp Thr Glu Leu
            980                 985                 990
Lys Val Asp Pro Phe Ser Phe Lys Thr Arg Ala Lys Ser Cys Gly Glu
            995                 1000                1005
Arg Asp Val Lys Gly Ile Arg Thr Leu Phe Leu Gly Ile Pro Asp Glu
    1010                1015                1020
Asn Phe Glu Asp His Ser Ala Pro Pro Ser Pro Glu Glu Lys Asp Ser
1025                1030                1035                1040
Gly Phe Phe Met Leu Arg Lys Asp Ser Glu Arg Arg Ala Thr Leu His
                1045                1050                1055
Arg Ile Leu Thr Glu Asp Gln Asp Lys Ile Val Arg Asn Leu Met Glu
        1060                1065                1070
Ser Leu Ala Gln Gly Ala Glu Glu Pro Lys Leu Lys Trp Glu His Ile
        1075                1080                1085
Thr Thr Leu Ile Ala Ser Leu Arg Glu Phe Val Arg Ser Thr Asp Arg
    1090                1095                1100
Lys Ile Ile Ala Thr Thr Leu Ser Lys Leu Lys Leu Glu Leu Asp Phe
1105                1110                1115                1120
Asp Ser His Gly Ile Ser Gln Val Gln Val Val Leu Phe Gly Phe Gln
                1125                1130                1135
Asp Ala Val Asn Lys Val Leu Arg Asn His Asn Ile Lys Pro His Trp
            1140                1145                1150
Met Phe Ala Leu Asp Ser Ile Ile Arg Lys Ala Val Gln Thr Ala Ile
            1155                1160                1165
Thr Ile Leu Val Pro Glu Leu Arg Pro His Phe Ser Leu Ala Ser Glu
        1170                1175                1180
Ser Asp Thr Ala Asp Gln Glu Asp Leu Asp Val Glu Asp Asp His Glu
1185                1190                1195                1200
Glu Gln Pro Ser Asn Gln Thr Val Arg Arg Pro Gln Ala Val Ile Glu
                1205                1210                1215
Asp Ala Val Ala Thr Ser Gly Val Ser Thr Leu Ser Ser Thr Val Ser
            1220                1225                1230
His Asp Ser Gln Ser Ala His Arg Ser Leu Asn Val Gln Leu Gly Arg
            1235                1240                1245
Met Lys Ile Glu Thr Asn Arg Leu Leu Glu Glu Leu Val Arg Lys Glu
    1250                1255                1260
```

```
Lys Glu Leu Gln Ala Leu Leu His Arg Ala Ile Glu Glu Lys Asp Gln
1265                1270                1275                1280

Glu Ile Lys His Leu Lys Leu Lys Ser Gln Pro Ile Glu Ile Pro Glu
            1285                1290                1295

Leu Pro Val Phe His Leu Asn Ser Ser Gly Thr Asn Ile Glu Asp Ser
        1300                1305                1310

Glu Leu Thr Asp Trp Leu Arg Val Asn Gly Ala Asp Glu Asp Thr Ile
    1315                1320                1325

Ser Arg Phe Leu Ala Glu Asp Tyr Thr Leu Leu Asp Val Leu Tyr Tyr
    1330                1335                1340

Val Thr Arg Asp Asp Leu Lys Cys Leu Arg Leu Arg Gly Gly Met Leu
1345                1350                1355                1360

Cys Thr Leu Trp Lys Ala Ile Ile Asp Phe Arg Asn Lys Gln Thr
            1365                1370                1375

<210> SEQ ID NO 2
<211> LENGTH: 4533
<212> TYPE: DNA
<213> ORGANISM: Homo sapiens
<220> FEATURE:
<221> NAME/KEY: CDS
<222> LOCATION: (268)..(4392)

<400> SEQUENCE: 2
acccggcttc cccacccctt gtactctaaa ctctgcagag ggcgagcgtg cggccacgga      60
ggcgccgagg aggagcgagc gccgccgggc agcggcgtgc cctcggggga gagggcgccg     120
gagaggaggc ggcggcgcgg cggcgagggc gcggcgcgcg atggcagctg cttagcccgg     180
cgggcgcgga gcagccccga gctgtggctg gccaggcggt gcggctgggc ggggacgcc      240 gccgccgttg ctgcccggcc cggagag atg agc acg gag gcg gac gag ggc atc    294
                              Met Ser Thr Glu Ala Asp Glu Gly Ile
                                1               5 act ttc tct gtg cca ccc ttc gcc ccc tcg ggc ttc tgc acc atc ccc      342
Thr Phe Ser Val Pro Pro Phe Ala Pro Ser Gly Phe Cys Thr Ile Pro
 10              15                  20                  25 gag ggc ggc atc tgc agg agg gga gga gcg gcg gcg gtg ggc gag ggc      390
Glu Gly Gly Ile Cys Arg Arg Gly Gly Ala Ala Ala Val Gly Glu Gly
             30                  35                  40 gag gag cac cag ctg cca ccg ccg ccg ggc agt ttc tgg aac gtg          438
Glu Glu His Gln Leu Pro Pro Pro Pro Gly Ser Phe Trp Asn Val
         45                  50                  55 gag agc gcc gct gcc cct ggc atc ggt tgt ccg gcg gcc acc tcc tcg      486
Glu Ser Ala Ala Ala Pro Gly Ile Gly Cys Pro Ala Ala Thr Ser Ser
     60                  65                  70 agc agt gcc acc cga ggc cgg ggc agc tct gtt ggc ggg ggc agc cga      534
Ser Ser Ala Thr Arg Gly Arg Gly Ser Ser Val Gly Gly Gly Ser Arg
 75                  80                  85 cgg acc acg gtg gca tat gtg atc aac gaa gcg agc caa ggg caa ctg      582
Arg Thr Thr Val Ala Tyr Val Ile Asn Glu Ala Ser Gln Gly Gln Leu
 90                  95                 100                 105 gtg gtg gcc gag agc gag gcc ctg cag agc ttg cgg gag gcg tgc gag      630
Val Val Ala Glu Ser Glu Ala Leu Gln Ser Leu Arg Glu Ala Cys Glu
             110                 115                 120 aca gtg ggc gcc acc ctg gaa acc ctg cat ttt ggg aaa ctc gac ttt      678
Thr Val Gly Ala Thr Leu Glu Thr Leu His Phe Gly Lys Leu Asp Phe
         125                 130                 135 gga gaa acc acc gtg ctg gac cgc ttt tac aat gca gat att gcg gtg      726
Gly Glu Thr Thr Val Leu Asp Arg Phe Tyr Asn Ala Asp Ile Ala Val
```

-continued

```
                140                 145                 150
gtg gag atg agc gat gcc ttc cgg cag ccg tcc ttg ttt tac cac ctt      774
Val Glu Met Ser Asp Ala Phe Arg Gln Pro Ser Leu Phe Tyr His Leu
    155                 160                 165 ggg gtg aga gaa agt ttc agc atg gcc aac aac atc atc ctc tac tgc      822
Gly Val Arg Glu Ser Phe Ser Met Ala Asn Asn Ile Ile Leu Tyr Cys
170                 175                 180                 185 gat act aac tcg gac tct ctg cag tca ctg aag gaa atc att tgc cag      870
Asp Thr Asn Ser Asp Ser Leu Gln Ser Leu Lys Glu Ile Ile Cys Gln
                    190                 195                 200 aag aat act atg tgc act ggg aac tac acc ttt gtt cct tac atg ata      918
Lys Asn Thr Met Cys Thr Gly Asn Tyr Thr Phe Val Pro Tyr Met Ile
                205                 210                 215 act cca cat aac aaa gtc tac tgc tgt gac agc agc ttc atg aag ggg      966
Thr Pro His Asn Lys Val Tyr Cys Cys Asp Ser Ser Phe Met Lys Gly
            220                 225                 230 ttg aca gag ctc atg caa ccg aac ttc gag ctg ctt ctt gga ccc atc     1014
Leu Thr Glu Leu Met Gln Pro Asn Phe Glu Leu Leu Leu Gly Pro Ile
    235                 240                 245 tgc tta cct ctt gtg gat cgt ttt att caa ctt ttg aag gtg gca caa     1062
Cys Leu Pro Leu Val Asp Arg Phe Ile Gln Leu Leu Lys Val Ala Gln
250                 255                 260                 265 gca agt tct agc cag tac ttc cgg gaa tct ata ctc aat gac atc agg     1110
Ala Ser Ser Ser Gln Tyr Phe Arg Glu Ser Ile Leu Asn Asp Ile Arg
                    270                 275                 280 aaa gct cgt aat tta tac act ggt aaa gaa ttg gca gct gag ttg gca     1158
Lys Ala Arg Asn Leu Tyr Thr Gly Lys Glu Leu Ala Ala Glu Leu Ala
                285                 290                 295 aga att cgg cag cga gta gat aat atc gaa gtc ttg aca gca gat att     1206
Arg Ile Arg Gln Arg Val Asp Asn Ile Glu Val Leu Thr Ala Asp Ile
            300                 305                 310 gtc ata aat ctg tta ctt tcc tac aga gat atc cag gac tat gat tct     1254
Val Ile Asn Leu Leu Leu Ser Tyr Arg Asp Ile Gln Asp Tyr Asp Ser
    315                 320                 325 att gtg aag ctg gta gag act tta gaa aaa ctg cca acc ttt gat ttg     1302
Ile Val Lys Leu Val Glu Thr Leu Glu Lys Leu Pro Thr Phe Asp Leu
330                 335                 340                 345 gcc tcc cat cac cat gtg aag ttt cat tat gca ttt gca ctg aat agg     1350
Ala Ser His His His Val Lys Phe His Tyr Ala Phe Ala Leu Asn Arg
                    350                 355                 360 aga aat ctc cct ggt gac aga gca aaa gct ctt gat att atg att ccc     1398
Arg Asn Leu Pro Gly Asp Arg Ala Lys Ala Leu Asp Ile Met Ile Pro
                365                 370                 375 atg gtg caa agc gaa gga caa gtt gct tca gat atg tat tgc cta gtt     1446
Met Val Gln Ser Glu Gly Gln Val Ala Ser Asp Met Tyr Cys Leu Val
            380                 385                 390 ggt cga atc tac aaa gat atg ttt ttg gac tct aat ttc acg gac act     1494
Gly Arg Ile Tyr Lys Asp Met Phe Leu Asp Ser Asn Phe Thr Asp Thr
    395                 400                 405 gaa agc aga gac cat gga gct tct tgg ttc aaa aag gca ttt gaa tct     1542
Glu Ser Arg Asp His Gly Ala Ser Trp Phe Lys Lys Ala Phe Glu Ser
410                 415                 420                 425 gag cca aca cta cag tca gga att aat tat gcg gtc ctc ctc ctg gca     1590
Glu Pro Thr Leu Gln Ser Gly Ile Asn Tyr Ala Val Leu Leu Leu Ala
                    430                 435                 440 gct gga cac cag ttt gaa tct tcc ttt gag ctc cgg aaa gtt ggg gtg     1638
Ala Gly His Gln Phe Glu Ser Ser Phe Glu Leu Arg Lys Val Gly Val
                445                 450                 455 aag cta agt agt ctt ctt ggt aaa aag gga aac ttg gaa aaa ctc cag     1686
```

```
                 Lys Leu Ser Ser Leu Leu Gly Lys Lys Gly Asn Leu Glu Lys Leu Gln
                         460                 465                 470 agc tac tgg gaa gtt gga ttt ttt ctg ggg gcc agc gtc cta gcc aat           1734
Ser Tyr Trp Glu Val Gly Phe Phe Leu Gly Ala Ser Val Leu Ala Asn
        475                 480                 485 gac cac atg aga gtc att caa gca tct gaa aag ctt ttt aaa ctg aag           1782
Asp His Met Arg Val Ile Gln Ala Ser Glu Lys Leu Phe Lys Leu Lys
490                 495                 500                 505 aca cca gca tgg tac ctc aag tct att gta gag aca att ttg ata tat           1830
Thr Pro Ala Trp Tyr Leu Lys Ser Ile Val Glu Thr Ile Leu Ile Tyr
                510                 515                 520 aag cat ttt gtg aaa ctg acc aca gaa cag cct gtg gcc aag caa gaa           1878
Lys His Phe Val Lys Leu Thr Thr Glu Gln Pro Val Ala Lys Gln Glu
            525                 530                 535 ctt gtg gac ttt tgg atg gat ttc ctg gtc gag gcc aca aag aca gat           1926
Leu Val Asp Phe Trp Met Asp Phe Leu Val Glu Ala Thr Lys Thr Asp
        540                 545                 550 gtt act gtg gtt agg ttt cca gta tta ata tta gaa cca acc aaa atc           1974
Val Thr Val Val Arg Phe Pro Val Leu Ile Leu Glu Pro Thr Lys Ile
555                 560                 565 tat caa cct tct tat ttg tct atc aac aat gaa gtt gag gaa aag aca           2022
Tyr Gln Pro Ser Tyr Leu Ser Ile Asn Asn Glu Val Glu Glu Lys Thr
570                 575                 580                 585 atc tct att tgg cac gtg ctt cct gat gac aag aaa ggt ata cat gag           2070
Ile Ser Ile Trp His Val Leu Pro Asp Asp Lys Lys Gly Ile His Glu
                590                 595                 600 tgg aat ttt agt gcc tct tct gtc agg gga gtg agt att tct aaa ttt           2118
Trp Asn Phe Ser Ala Ser Ser Val Arg Gly Val Ser Ile Ser Lys Phe
            605                 610                 615 gaa gaa aga tgc tgc ttt ctt tat gtg ctt cac aat tct gat gat ttc           2166
Glu Glu Arg Cys Cys Phe Leu Tyr Val Leu His Asn Ser Asp Asp Phe
        620                 625                 630 caa atc tat ttc tgt aca gaa ctt cat tgt aaa aag ttt ttt gag atg           2214
Gln Ile Tyr Phe Cys Thr Glu Leu His Cys Lys Lys Phe Phe Glu Met
635                 640                 645 gtg aac acc att acc gaa gag aag ggg aga agc aca gag gaa gga gac           2262
Val Asn Thr Ile Thr Glu Glu Lys Gly Arg Ser Thr Glu Glu Gly Asp
650                 655                 660                 665 tgt gaa agt gac ttg ctg gag tat gac tat gaa tat gat gaa aat ggt           2310
Cys Glu Ser Asp Leu Leu Glu Tyr Asp Tyr Glu Tyr Asp Glu Asn Gly
                670                 675                 680 gac aga gtc gtt tta gga aaa ggc act tat ggg ata gtc tac gca ggt           2358
Asp Arg Val Val Leu Gly Lys Gly Thr Tyr Gly Ile Val Tyr Ala Gly
            685                 690                 695 cgg gac ttg agc aac caa gtc aga att gct att aag gaa atc cca gag           2406
Arg Asp Leu Ser Asn Gln Val Arg Ile Ala Ile Lys Glu Ile Pro Glu
        700                 705                 710 aga gac agc aga tac tct cag ccc ctg cat gaa gaa ata gca ttg cat           2454
Arg Asp Ser Arg Tyr Ser Gln Pro Leu His Glu Glu Ile Ala Leu His
715                 720                 725 aaa cac ctg aag cac aaa aat att gtc cag tat ctg ggc tct ttc agt           2502
Lys His Leu Lys His Lys Asn Ile Val Gln Tyr Leu Gly Ser Phe Ser
730                 735                 740                 745 gag aat ggt ttc att aaa atc ttc atg gag cag gtc cct gga gga agt           2550
Glu Asn Gly Phe Ile Lys Ile Phe Met Glu Gln Val Pro Gly Gly Ser
                750                 755                 760 ctt tat gct ctc ctt cgt tcc aaa tgg ggt cca tta aaa gac aat gag           2598
Leu Tyr Ala Leu Leu Arg Ser Lys Trp Gly Pro Leu Lys Asp Asn Glu
            765                 770                 775
```

-continued

| | |
|---|---|
| caa aca att ggc ttt tat aca aag caa ata ctg gaa gga tta aaa tat<br>Gln Thr Ile Gly Phe Tyr Thr Lys Gln Ile Leu Glu Gly Leu Lys Tyr<br>780       785       790 | 2646 |
| ctc cat gac aat cag ata gtt cac cgg gac ata aag ggt gac aat gtg<br>Leu His Asp Asn Gln Ile Val His Arg Asp Ile Lys Gly Asp Asn Val<br>  795       800       805 | 2694 |
| ttg att aat acc tac agt ggt gtt ctc aag atc tct gac ttc gga aca<br>Leu Ile Asn Thr Tyr Ser Gly Val Leu Lys Ile Ser Asp Phe Gly Thr<br>810       815       820       825 | 2742 |
| tca aag agg ctt gct ggc ata aac ccc tgt act gaa act ttt act ggt<br>Ser Lys Arg Leu Ala Gly Ile Asn Pro Cys Thr Glu Thr Phe Thr Gly<br>    830       835       840 | 2790 |
| acc ctc cag tat atg gca cca gaa ata ata gat aaa gga cca aga ggc<br>Thr Leu Gln Tyr Met Ala Pro Glu Ile Ile Asp Lys Gly Pro Arg Gly<br>    845       850       855 | 2838 |
| tac gga aaa gca gca gac atc tgg tct ctg ggc tgt aca atc att gaa<br>Tyr Gly Lys Ala Ala Asp Ile Trp Ser Leu Gly Cys Thr Ile Ile Glu<br>860       865       870 | 2886 |
| atg gcc aca gga aaa ccc cca ttt tat gaa ctg gga gaa cca caa gca<br>Met Ala Thr Gly Lys Pro Pro Phe Tyr Glu Leu Gly Glu Pro Gln Ala<br>875       880       885 | 2934 |
| gct atg ttc aag gtg gga atg ttt aaa gtc cac cct gag atc cca gag<br>Ala Met Phe Lys Val Gly Met Phe Lys Val His Pro Glu Ile Pro Glu<br>890       895       900      905 | 2982 |
| tcc atg tct gca gag gcc aag gca ttc ata ctg aaa tgt ttt gaa cca<br>Ser Met Ser Ala Glu Ala Lys Ala Phe Ile Leu Lys Cys Phe Glu Pro<br>    910       915       920 | 3030 |
| gat cct gac aag aga gcc tgt gct aac gac ttg ctt gtt gat gag ttt<br>Asp Pro Asp Lys Arg Ala Cys Ala Asn Asp Leu Leu Val Asp Glu Phe<br>  925       930       935 | 3078 |
| tta aaa gtt tca agc aaa aag aaa aag aca caa cct aag ctt tca gct<br>Leu Lys Val Ser Ser Lys Lys Lys Lys Thr Gln Pro Lys Leu Ser Ala<br>940       945       950 | 3126 |
| ctt tca gct gga tca aat gca gaa tat ctc agg agt ata tcc ttg ccg<br>Leu Ser Ala Gly Ser Asn Ala Glu Tyr Leu Arg Ser Ile Ser Leu Pro<br>955       960       965 | 3174 |
| gta cct gtg ctg gtg gag gac acc agc agc agc agt gag tac ggc tca<br>Val Pro Val Leu Val Glu Asp Thr Ser Ser Ser Ser Glu Tyr Gly Ser<br>970       975       980      985 | 3222 |
| gtt tca ccc gac acg gag ttg aaa gtg gac ccc ttc tct ttc aaa aca<br>Val Ser Pro Asp Thr Glu Leu Lys Val Asp Pro Phe Ser Phe Lys Thr<br>    990       995       1000 | 3270 |
| aga gcc aag tcc tgc gga gaa aga gat gtc aag gga att cgg aca ctc<br>Arg Ala Lys Ser Cys Gly Glu Arg Asp Val Lys Gly Ile Arg Thr Leu<br>    1005       1010      1015 | 3318 |
| ttt ttg ggc att cca gat gag aat ttt gaa gat cac agt gct cct cct<br>Phe Leu Gly Ile Pro Asp Glu Asn Phe Glu Asp His Ser Ala Pro Pro<br>    1020       1025      1030 | 3366 |
| tcc cct gaa gaa aaa gat tct gga ttc ttc atg ctg agg aag gac agt<br>Ser Pro Glu Glu Lys Asp Ser Gly Phe Phe Met Leu Arg Lys Asp Ser<br>1035       1040      1045 | 3414 |
| gag agg cga gct acc ctt cac agg atc ctg acg gaa gac caa gac aaa<br>Glu Arg Arg Ala Thr Leu His Arg Ile Leu Thr Glu Asp Gln Asp Lys<br>1050      1055      1060      1065 | 3462 |
| att gtg aga aac cta atg gaa tct tta gct cag ggg gct gaa gaa ccg<br>Ile Val Arg Asn Leu Met Glu Ser Leu Ala Gln Gly Ala Glu Glu Pro<br>    1070       1075      1080 | 3510 |
| aaa cta aaa tgg gaa cac atc aca acc ctc att gca agc ctc aga gaa<br>Lys Leu Lys Trp Glu His Ile Thr Thr Leu Ile Ala Ser Leu Arg Glu<br>    1085       1090      1095 | 3558 |

```
ttt gtg aga tcc act gac cga aaa atc ata gcc acc aca ctg tca aag    3606
Phe Val Arg Ser Thr Asp Arg Lys Ile Ile Ala Thr Thr Leu Ser Lys
        1100                1105                1110 ctg aaa ctg gag ctg gac ttc gac agc cat ggc att agc caa gtc cag    3654
Leu Lys Leu Glu Leu Asp Phe Asp Ser His Gly Ile Ser Gln Val Gln
    1115                1120                1125 gtg gta ctc ttt ggt ttt caa gat gct gtc aat aaa gtt ctt cgg aat    3702
Val Leu Phe Gly Phe Gln Asp Ala Val Asn Lys Val Leu Arg Asn
1130                1135                1140                1145 cat aac atc aag ccg cac tgg atg ttt gcc tta gac agt atc att cgg    3750
His Asn Ile Lys Pro His Trp Met Phe Ala Leu Asp Ser Ile Ile Arg
            1150                1155                1160 aag gcg gta cag aca gcc att acc atc ctg gtt cca gaa cta agg cca    3798
Lys Ala Val Gln Thr Ala Ile Thr Ile Leu Val Pro Glu Leu Arg Pro
        1165                1170                1175 cat ttc agc ctt gca tct gag agt gat act gct gat caa gaa gac ttg    3846
His Phe Ser Leu Ala Ser Glu Ser Asp Thr Ala Asp Gln Glu Asp Leu
    1180                1185                1190 gat gta gaa gat gac cat gag gaa cag cct tca aat caa act gtc cga    3894
Asp Val Glu Asp Asp His Glu Glu Gln Pro Ser Asn Gln Thr Val Arg
    1195                1200                1205 aga cct cag gct gtc att gaa gat gct gtg gct acc tca ggc gtg agc    3942
Arg Pro Gln Ala Val Ile Glu Asp Ala Val Ala Thr Ser Gly Val Ser
1210                1215                1220                1225 acg ctc agt tct act gtg tct cat gat tcc cag agt gct cac cgg tca    3990
Thr Leu Ser Ser Thr Val Ser His Asp Ser Gln Ser Ala His Arg Ser
            1230                1235                1240 ctg aat gta cag ctt gga agg atg aaa ata gaa acc aat aga tta ctg    4038
Leu Asn Val Gln Leu Gly Arg Met Lys Ile Glu Thr Asn Arg Leu Leu
        1245                1250                1255 gaa gaa ttg gtt cgg aaa gag aaa gaa tta caa gca ctc ctt cat cga    4086
Glu Glu Leu Val Arg Lys Glu Lys Glu Leu Gln Ala Leu Leu His Arg
    1260                1265                1270 gct att gaa gaa aaa gac caa gaa att aaa cac ctg aag ctt aag tcc    4134
Ala Ile Glu Glu Lys Asp Gln Glu Ile Lys His Leu Lys Leu Lys Ser
    1275                1280                1285 caa ccc ata gaa att cct gaa ttg cct gta ttt cat cta aat tct tct    4182
Gln Pro Ile Glu Ile Pro Glu Leu Pro Val Phe His Leu Asn Ser Ser
1290                1295                1300                1305 ggc aca aat att gaa gat tct gaa ctt acc gac tgg ctg aga gtg aat    4230
Gly Thr Asn Ile Glu Asp Ser Glu Leu Thr Asp Trp Leu Arg Val Asn
            1310                1315                1320 gga gct gat gaa gac act ata agc cgg ttt ttg gct gaa gat tat aca    4278
Gly Ala Asp Glu Asp Thr Ile Ser Arg Phe Leu Ala Glu Asp Tyr Thr
        1325                1330                1335 cta ttg gat gtt ctc tac tat gtt aca cgt gat gac tta aaa tgc ttg    4326
Leu Leu Asp Val Leu Tyr Tyr Val Thr Arg Asp Asp Leu Lys Cys Leu
    1340                1345                1350 aga cta agg gga ggg atg ctg tgc aca ctg tgg aag gct atc att gac    4374
Arg Leu Arg Gly Gly Met Leu Cys Thr Leu Trp Lys Ala Ile Ile Asp
    1355                1360                1365 ttt cga aac aaa cag act tgactgttgc tcaatctaat cttcgatgga           4422
Phe Arg Asn Lys Gln Thr
1370                1375 aattctaaaa attaatacag agctgatctt cttgggggtg ggaaaatcga agggagagga    4482
gaaaggcgct gcactttaaa tccagtattt gtttactcat gttaaaaaaa a            4533

<210> SEQ ID NO 3
```

```
<211> LENGTH: 16
<212> TYPE: PRT
<213> ORGANISM: Homo sapiens

<400> SEQUENCE: 3

Thr Glu Glu Lys Gly Arg Ser Thr Glu Glu Gly Asp Cys Glu Ser Asp
 1               5                  10                  15
```

APOPTOSIS-INDUCING PROTEIN AND GENE ENCODING THE SAME

This application is a national stage entry of PCT/JP97/01348 issued on Apr. 18, 1997.

BACKGROUND OF THE INVENTION

1. Field of the Invention

The present invention relates to a protein which induces apoptosis (cell death), a gene encoding the same, and a therapeutic agent for malignant tumors.

2. Background Art

The mitogen-activated protein (MAP) kinase signaling cascade, a signal transduction pathway well conserved in cells from yeasts to vertebrates, consists of three distinct members of the protein kinase family, including MAP kinase (MAPK), MAPK kinase (MAPKK), and MAPKK kinase (MAPKKK) (T. Sturgill & J. Wu, Biochim. Biophys. Acta. 1092, 350, 1991; E. Nishida & Y. Gotoh, Trends Biochem. Sci., 18, 128, 1993; B. Errede & D. Levin, Curr. Opin. Cell Biol., 5, 254, 1993; C. Marshall, Curr. Opin. Genet. Dev., 4, 82, 1994). MAPKKK phosphorylates and thereby activates MAPKK, and the activated form of MAPKK in turn phosphorylates and activates MAPK. Activated MAPK translocates to the cell nucleus and regulates the activities of transcription factors and thereby controls expression of various genes (T. Sturgill & J. Wu, Biochim. Biophys. Acta, 1092, 350, 1991; E. Nishida & Y. Gotoh, Trends Biochem. Sci., 18, 128, 1993; B. Errede & D. Levin, Curr. Opin. Cell Biol., 5, 254, 1993; C. Marshall, Curr. Opin. Genet. Dev., 4, 82, 1994).

Recent studies on MAPK signal transduction pathways have shown that at least two distinct MAPKKK-MAPKK-MAPK signal transduction pathways function in mammalian cells (R. Davis, Trends Biochem. Sci., 19, 470, 1994; A. Waskiewicz & J. Cooper, Curr. Opin. Cell Biol., 7, 798, 1995; J. Kyriakis & J. Avruch, J. Biol. Chem., 265, 17355, 1990; B. Derijard et al., Cell, 76, 1025, 1994; M. Yan et al., Nature, 372, 798, 1994; K. Yamaguchi et al., Science, 270, 2008, 1995; J. Kyriakis et al., Nature, 369, 156, 1994; I. Sanchez et al., Nature, 372, 794, 1994; B.

Derijard et al. Science, 267, 682, 1995; S. Matsuda et al., J.

Biol. Chem., 270, 12781, 1995). These two pathways each consist of the Raf-MAPKK-MAPK pathway and the MEKK-SEK1 (or MKK4)-SAPK (or JNK) pathway.

MKK3/MAPKK6 (or MKK6, a close relative of MKK3) and p38 protein kinase are protein kinases corresponding to MAPKK and MAPK, respectively, and are known to form another MAPK signal transduction pathway (R. Davis, Trends Biochem. Sci., 19, 470, 1994; A. Waskiewicz & J. Cooper, Curr. Opin. Cell Biol., 7, 798, 1995; J. Han et al., J. Biol. Chem., 271, 2886, 1996; J. Raingeaud et al., Mol. Cell. Biol., 16, 1247, 1996; T. Moriguchi et al., J. Biol. Chem., 271, 13675, 1996).

Recent studies suggest that the SAPK and/or p38 MAP kinase signaling cascades are involved in at least a part of the signal transduction pathways which induce apoptosis (Z. Xia et al., Science, 270, 1326, 1995; Y. -R. Chen et al., J. Biol. Chem., 271, 631, 1996; N. Johnson et al., J. Biol. Chem., 271, 3229, 1996; M. Verheij et al., Nature, 380, 75, 1996). Apoptosis herein means cell death different from necrosis, namely program cell death. In apoptosis, DNA in each nucleosome is fragmented and the fragmented DNAs can be observed like a ladder by electrophoresis. Furthermore, apoptosis is considered to be involved in autoimmune diseases, HIV infection, neurotic diseases, hepatitis, leukemia, renal diseases, skin diseases, eye diseases and aging as well as cancer degeneration ("Forefront of Research on Apoptosis." Ed. Masayuki Miura, Shigenobu Toya and Sadatoshi Kizaki, Experimental Medicine, Vol. 13, 1995).

Tumor necrosis factor-α (TNF-α) is known to be a strong cellular apoptosis initiation substance. A recent study has shown that such cellular apoptosis initiation substances activate the SAPK signal transduction system (J. Kyriakis et al., Nature, 372, 794, 1994; J. Raingeaud et al., J. Biol. Chem., 270, 7420, 1995).

However, as far as the inventors know, proteins corresponding to MAPKKK present in upstream of the MKK3-p38 pathway and the SEK1-SAPK pathway, mechanisms of activation of these pathways, and mechanisms of apoptosis through these pathways have not been reprted.

SUMMARY OF THE INVENTION

The inventors have now identified a novel mammalian protein (ASK1) corresponding to MAPKKK, which activates the MKK3-p38 signal transduction pathway as well as the SEK1-SAPK signal transduction pathway. The inventors have also found that proinflammatory cytokines activate ASK1 and the activated ASK1 is involved in cellular induction of apoptosis through the SEK1-SAPK and MKK3-p38 signaling cascades. Furthermore, the inventors found that a dominant-negative mutant of ASK1 inhibits apoptosis induced by TNF-α. The present invention is based on these findings.

Accordingly, an object of the present invention is to provide a protein which induces apoptosis, a base sequence encoding the protein, a vector comprising the base sequence, a host comprising the vector and a method for producing the protein.

Another object of the present invention is to provide an agent for use in the treatment of malignant tumors or a gene therapy agent for use in the treatment of malignant tumors.

A further object of the present invention is to provide a partial peptide of the apoptosis-inducing protein and an antibody against the apoptosis-inducing protein.

The protein according to the present invention is a protein which has a protein kinase activity and enhances the SEK1 kinase activity and/or MKK3 kinase activity, or derivatives thereof.

BRIEF DESCRIPTION OF DRAWINGS

FIG. 1 shows the deduced amino acid sequence of human ASK1. The putative translation start sites for two independent clones (clone 20 and clone 27) are indicated by arrows. The protein kinase domain is shown in boldface. An FKBP-type peptidyl-prolyl cis-trans isomerase motif present in the N-terminal non-catalytic portion is underlined. Abbreviations for the amino acid residues are as follows: A, Ala: C, Cys; D, Asp; E, Glu; F, Phe; G, Gly; H: His; I: Ile; K: Lys; L: Leu; M: Met; N: Asn; P: Pro; Q: Gln; R: Arg; S, Ser; T, Thr; V, Val; W, Trp; and Y, Tyr.

FIG. 2 shows the phylogenetic relationship of the MAP-KKK family.

FIG. 3 shows RNA blots (electrophoretic photographs) demonstrating tissue distribution of ASK1.

FIG. 6 is an electrophoretic photograph showing in vitro activation of MAPKKs by ASK1. COS7 cells were transfected with pcDNA3-ASK1 and cell lysates were subjected to immunoprecipitation with preimmune serum (Mock ppt) or antiserum to ASK1 (ASK1 ppt). The immune complex or a buffer solution (Buffer) was first incubated with (+) or without (−) His-MAPKK, His-SEK1, His-MKK3, or His-MAPKK6 MAPKK, and then the kinase activity of individual MAPKK was measured with the substrate GST-kinase-negative MAPK for MAPKK and His-kinase negative MPK2 for SEK1, MKK3, and MAPKK6. In the photograph, "KN-MAPK" represents GST-kinase negative MAPK and "KN-MPK2" represents His-kinase negative MPK2.

FIG. 8 is a graph showing ASK1-dependent inhibition of [$^3$H] thymidine incorporation. ■: Vector alone, ●: ASK1, ○: ASK1 (K709R). This data represents three independent experiments. Error bars represent the standard deviations.

FIG. 9 is an electrophoretic photograph showing dose-dependent ASK1 protein expression (top) and ASK1 activation (bottom) by $ZnCl_2$ induction. "no-IP" represents the case where the cell lysate was used as an enzyme sample without immunoprecipitation.

FIG. 11 shows phase-contrast microscopic photographs of representative cell morphology taken at the same magnification. These photographs show ASK1-dependent cell death. (Top) Cells were incubated in an MEM medium containing 1% FBS in the presence or absence of 100 μM $ZnCl_2$ for 26 hours. (Bottom) Cells were incubated in an MEM medium without FBS in the presence or absence of 100 μM $ZnCl_2$ for 25 hours. The cells were then stained by the TUNEL method. Apoptotic cells are shown by dark brown staining. Photographs were taken at a higher magnification than in the top panel.

FIG. 14 shows TNF-α dose-dependent activation of ASK1. Values for ASK1 activity are the averages from at least five independent experiments. Error bars indicate the standard deviations.

FIG. 15 is an electrophoretic photograph showing that DNA fragmentation in 298 cells stimulated by TNF-α in the presence or absence (none) of actinomycin D is inhibited by transfection of ASK1(K709R).

DETAILED DESCRIPTION OF THE INVENTION

Definition

Figure 4:
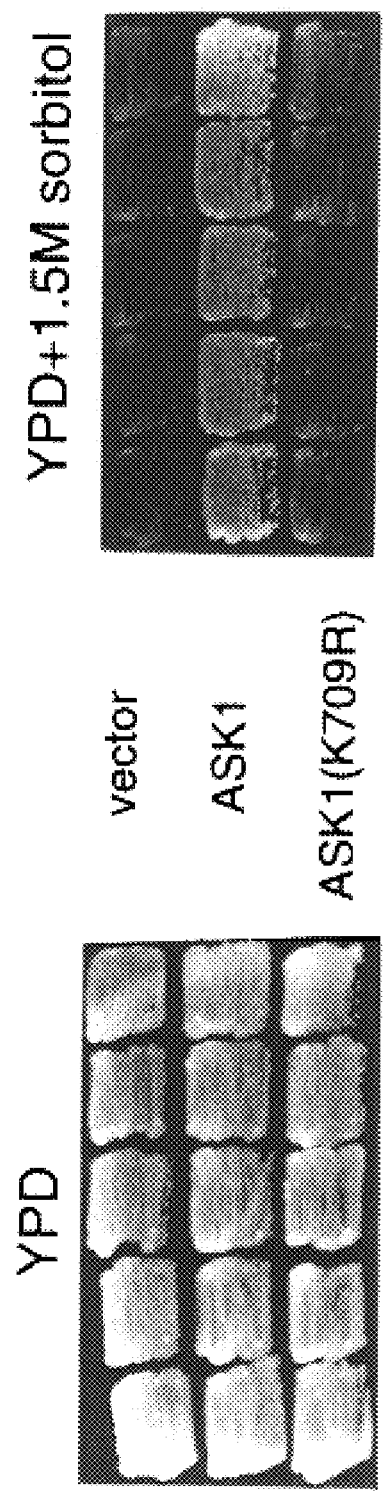
FIG. 4 shows photographs demonstrating the growth (colony formation) of yeast mutant strain TM257-H1 with ASK1 gene expression (ASK1, ASK1(K709R)) or without ASK1 gene expression (vector). Tests were carried out in the presence or absence of 1.5 M sorbitol.

The term "amino acid" in the present invention includes both optical isomers, i.e., the L-isomer and the D-isomer. Thus, the term "protein" herein means not only proteins constituted solely by L-amino acids but also proteins comprising D-amino acids in part or in total.

Furthermore, the term "amino acid" herein includes not only the twenty α-amino acids which constitute natural proteins but also other α-amino acids as well as β-, γ, and δ-amino acids, non-natural amino acids, and the like. Thus, amino acids with which proteins are substituted or amino acids inserted into proteins as shown below are not restricted to the twenty α-amino acids which constitute natural proteins but may be other α-amino acids as well as β-, γ- and δ-amino acids, non-natural amino acids, and the like. Such β-, γ and δ-amino acids include β-alanine, γ-aminobutyric acid or ornithine. The amino acids other than those constituting natural proteins, or the non-natural amino acids include 3,4-dihydroxyphenylalanine, phenylglycine, cyclohexylglycine, 1,2,3,4-tetrahydroisoquinoline-3-carboxylic acid or nipecotinic acid.

In this specification, a specific mutation is notated by the original amino acid residue (one letter) first, the position number second and the amino acid residue after substitution (one letter) third. For example, "K709R" means K (Lys: lysine), the amino residue at position 709, is substituted by R (Arg: arginine).

The term "protein" as used herein includes peptides. Furthermore, the expression "protein according to the present invention" includes derivatives of the protein.

Apoptosis-inducing Protein

The apoptosis-inducing protein according to the present invention is a protein which has a protein kinase catalytic region and enhances SEK1 kinase activity and/or M3 kinase activity, or derivatives thereof.

The apoptosis-inducing protein is not specifically restricted to any source but it may be derived from a mammal including a human, or any other sources.

The apoptosis-inducing protein has protein kinase activity. The term "protein having protein kinase activity" in the present invention means a protein which is evaluated by those skilled in the art to have protein kinase activity, for example, a protein which is evaluated to have protein kinase activity when examined under the same conditions as in Example 1. The term "protein kinase activity" includes serine/threonine protein kinase activity.

The apoptosis-inducing protein enhances the SEK1 kinase activity and/or MKK3 kinase activity. The term "protein enhancing the SEK1 kinase activity and/or M3 kinase activity" in the present invention means a protein which is evaluated by those skilled in the art to enhance these activities, for example, a protein which is evaluated to enhance the SEK1 kinase activity and/or MKK3 kinase activity when examined under the same conditions as in Examples 3, 4 and 6.

The protein according to the present invention is characterized by the induction of apoptosis. This apoptosis is mediated through the enhancement of the SAPK or JNK and/or p38 activity.

The enhancement of the SEK1 kinase activity and/or MKK3 kinase activity by the protein according to the present invention is accelerated by tumor necrosis factors (TNFs). An example of the tumor necrosis factor herein is TNF-α.

The term "derivatives of proteins" as used herein includes proteins in which the amino groups at the amino terminals (N-terminals) or all or a part of the amino groups of the side chains of the amino acids, and/or the carboxyl groups at the carboxyl terminals (C-terminals) or all or a part of the carboxyl groups of the side chains of the amino acids, and/or the functional groups other than the amino groups and carboxyl groups of the side chains of the amino acids (e.g., hydrogen, thiol group and amido group) have been modified by other appropriate substituents. The modification by other appropriate substituents is carried out, for example, to protect functional groups in the protein, to improve safety and tissue-translocation of the protein or to enhance protein activity.

The derivatives of the proteins include:
(1) proteins in which a part or all of the hydrogen atoms of the amino groups at the amino terminals (N-terminals) or the amino groups of the side chains of the amino acids are replaced by substituted or unsubstituted alkyl groups (which may be straight chain, branched chain, or cyclic) (e.g., methyl group, ethyl group, propyl group, isopropyl group, isobutyl group, butyl group, t-butyl group, cyclopropyl group, cyclohexyl, and benzyl group), substituted or unsubstituted acyl groups (e.g., formyl group, acetyl group, caproyl group, cyclohexylcarbonyl group, benzoyl group, phthaloyl group, tosyl group, nicotinoyl group, and piperidinecarbonyl group), urethane-type protective groups (e.g., p-nitrobenzyloxycarbonyl group, p-methoxybenzyloxycarbonyl group, p-biphenylisopropyl-oxycarbonyl group, and t-butoxycarbonyl group), or urea-type substituents (e.g., methylaminocarbonyl group, phenylcarbonyl group, and cyclohexylaminocarbonyl group).
(2) proteins in which a part or all of the carboxyl groups at the carboxyl terminals (C-terminals) or the carboxyl group of the side chains of the amino acids are esterified (for example, the hydrogen atom(s) are replaced by a methyl group, ethyl group, isopropyl group, cyclohexyl group, phenyl group, benzyl group, t-butyl group, or 4-picolyl group), or amidated (for example, unsubstituted amides or C1–C6 alkyl amides (e.g., methylamides, ethylamides and isopropylamides) are formed); and
(3) proteins in which a part or all of the functional groups other than the amino groups and carboxyl groups of the side chains of the amino acids (e.g., hydrogen, thiol group and amino group) are modified by substituents similar to those for the abovementioned amino groups or a trityl group.

Examples of the protein according to the present invention include proteins comprising the amino acid sequence of SEQ ID NO: 1 having one or more additions, insertions, substitutions and/or deletions, which have protein kinase activity and which enhance SEK1 kinase activity and/or MKK3 kinase activity. The terms "addition," "insertion," "substitution" and "deletion" as used herein refer to those that do not damage the capacity to enhance the protein kinase activity and SEK1 kinase activity and/or MKK3 kinase activity of the protein comprising the amino acid sequence of SEQ ID NO: 1. One or more additions, insertions, substitutions and deletions can be introduced.

The protein according to the present invention is characterized by the enhancement of the SEK1 kinase activity and/or MKK3 kinase activity. SEK1 and MKK3 are known to be involved in apoptosis. Therefore, the protein according to the present invention is useful in elucidating the mechanisms of cell functions such as apoptosis.

The present invention provides a protein comprising the amino acid sequence of SEQ ID NO: 1 having one or more additions, insertions, substitutions and/or deletions and lacking protein kinase activity, or a derivative thereof, (dominant-negative mutants). One or more additions, insertions, substitutions and deletions can be introduced.

This protein can be obtained by modifying a protein which has protein kinase activity and enhances SEK1 kinase activity and/or MKK3 kinase activity in such a manner so as to destroy the protein kinase activity. An example of such modification is a substitution: K709R.

This modified protein inhibits apoptosis caused by TNF-α as described in Examples thereinafter. Therefore, this modified protein is useful in elucidating the living phenomena in which ASK1 is involved in.

Base Sequence

The present invention provides a base sequence encoding the protein according to the present invention. An example of the base sequence encoding the protein according to the present invention is a sequence having a part or all of the DNA sequence of SEQ ID NO: 2. Base sequences in this specification mean both DNA sequences and RNA sequences.

When the modified amino acid sequence is given, the base sequence encoding such amino acid sequence is easily determined, and a variety of base sequences encoding the amino acid sequence described in SEQ ID NO: 1 can be selected. The base sequence encoding the protein according to the present invention thus means, in addition to a part or all of the DNA sequence described in SEQ ID NO: 2, another sequence encoding the same amino acid sequence and having degenerate codon(s) in the DNA sequence. Furthermore, this base sequence includes RNA sequences corresponding to such DNA sequences.

The base sequence according to the present invention may be derived naturally or obtained entirely by synthesis. It may also be synthesized using a part of a naturally occurring sequence. DNAs may typically be obtained by screening a chromosome library or a cDNA library in accordance with a conventional manner in the field of genetic engineering, for example, by screening with an appropriate DNA probe obtained based on information of the partial amino acid sequence.

Examples of the base sequence encoding the protein according to the present invention include the DNA sequence 268–4392 of SEQ ID NO: 2 (corresponding to the open reading frame).

Vector and Transformed Host Cell

The present invention provides a vector comprising the abovementioned base sequence in such a manner that the vector can be replicable and express the protein encoded by the base sequence in a host cell. In addition, the present invention provides a host cell transformed by this vector. This host-vector system is not particularly restricted and fusion protein expression systems with other proteins can also be used. Examples of the fusion protein expression system include those using MBP (maltose binding protein), GST (glutathione-S-transferase), HA (hemagglutinin), His (hexahistidine), myc, Fas, and the like.

Examples of the vector include plasmid vectors (e.g., expression vectors for prokaryotic cells, yeasts, insect cells, and animal cells), virus vectors (e.g., retrovirus vectors, adenovirus vectors, adeno-associated virus vectors, herpesvirus vectors, Sendai virus vectors, HIV vectors, and vaccinia virus vectors), and liposome vectors (e.g., cationic liposome vectors).

In order to express a desired amino acid sequence practically by introducing the vector according to the present invention into a host cell, the vector may contain, in addition to the base sequence according to the present invention, other sequences for controlling the expression (e.g., promoter sequences, terminator sequences and enhancer sequences) and gene markers for selecting microorganisms, insect cells, animal culture cells, or the like (e.g., neomycin resistance genes and kanamycin resistance genes). Furthermore, the vector may contain the base sequence according to the present invention in a repeated form (e.g., in tandem). These base sequences may also be introduced in a vector according to the conventional manner, and microorganisms, insect cells, animal cultured cells, or the like may be transformed by the vector based on the method conventionally used in this field.

The vector according to the present invention may be constructed based on the procedure and manner which have been conventionally used in the field of genetic engineering.

Furthermore, examples of the host cell include *Escherichia coli*, yeasts, insect cells and animal cells such as COS cells (e.g., COS7 cells), mink lung epithelial cells (e.g., Mv1Lu), lymphocytes, fibroblasts, CHO cells, blood cells, tumor cells, and the like.

The transformed host cells are cultured in an appropriate medium, and the protein according to the present invention may be obtained from the culture product. Thus, another aspect of the present invention provides a process for preparing the protein according to the present invention. The culture of the transformed host cell and culture conditions may be essentially the same as those for the cell to be used. In addition, the protein according to the present invention may be recovered from the culture medium and purified in the conventional manner.

The present invention can be applied in the gene therapy of malignant tumors (e.g., leukemia cells, digestive tract carcinoma cell, lung carcinoma cells, pancreas carcinoma cells, ovary carcinoma cells, uterus carcinoma cells, melanoma cells, brain tumor cells, etc.) by introducing a vector having the base sequence according to the present invention into cancer cells of an organism including humans using an appropriate method to express the protein according to the present invention, i.e., by transforming the cancer cells of cancer patients in situ. For example, when the protein according to the present invention is expressed in an organism including humans, in particular, in malignant tumor cells, apoptosis is induced causing the malignant tumor to shrink, thereby enabling treatment of the tumor (see Example 5).

As for the vectors for gene therapy, see Fumimaro Takahisa, Experimental Medicine (extra edition), Vol. 12, No. 15, "Forefront of Gene Therapy" (1994).

Use and Pharmaceutical Composition

The protein according to the present invention has protein kinase activity and enhances SEK1 kinase activity and/or MKK3 kinase activity (Examples 3 and 4). Furthermore, the protein according to the present invention induces apoptosis of immortalized cells (Example 5). Thus, the protein according to the present invention is useful in suppressing tumorigenesis and/or metastasis in malignant tumors.

Therefore, according to the present invention, an agent for use in the treatment of malignant tumors comprising the protein according to the present invention and a pharmaceutically acceptable carrier is provided. The term "treatment" in the present invention also refers to "prevention." Examples of malignant tumors include leukemia (for example, myelocytic leukemia, lymphocytic leukemia such as Burkitt lymphoma), digestive tract carcinoma, lung carcinoma, pancreas carcinoma, ovary carcinoma, uterus carcinoma, brain tumor, malignant melanoma, other carcinomas, and sarcomas.

The agent for use in the treatment of malignant tumors according to the present invention may be administered orally or parenterally (e.g., intramuscular injection, intravenous injection, subcutaneous administration, rectal administration, transdermal administration, nasal administration, and the like), preferably orally. The pharmaceutical agent may be administered to a human and other animals in a variety of dosage forms suited for oral or parenteral administration.

The agent for use in the treatment of malignant tumors can be formulated in a variety of form including oral agents such as tablets, capsules, granules, dispersible powders, pills, fine particles and troches, injections such as intravenous injections and intramuscular injections, rectal agents, fatty suppositories and aqueous suppositories, for example, depending on their intended uses. These preparations may be prepared according to methods well known in the art with conventional excipients, fillers, binding agents, wetting agents, disintegrating agents, surfactants, lubricants, dispersing agents, buffering agents, preservatives, dissolution aids, antiseptics, flavorings, analgesic agents and stabilizing agents. Examples of the abovementioned possible nontoxic additives to be used include lactose, fructose, glucose, starch, gelatin, magnesium carbonate, synthetic magnesium silicate, talc, magnesium stearate, methylcellulose, carboxymethylcellulose or a salt thereof, gum arabic, polyethylene glycol, syrup, Vaseline, glycerine, ethanol, propylene glycol, citric acid, sodium chloride, sodium sulfite, and sodium phosphate.

The content of the protein according to the present invention in a pharmaceutical agent varies depending on its dosage forms. The composition may contain about 1–50% by weight, preferably about 1–20% by weight, of the protein.

The dose of the protein for the treatment of malignant tumors may appropriately be determined in consideration of its uses and the age, sex and condition of a patient, and is desirably in the range of about 0.1–500 mg, preferably about 0.5–50 mg, per day for an adult, which may be administered at once or divided into several portions a day.

According to the present invention, a base sequence encoding the protein according to the present invention or a vector comprising the base sequence may be used to suppress tumorigenesis and/or metastasis of malignant tumors by transforming a target cell. In other words, the base sequence and vector can be used as a gene therapeutic agent for use in the treatment of malignant tumors (the gene therapy agent). The method of administration, effective dosage, possible carriers to be included, and other parameters of a gene therapeutic agent can conform to those for an antitumor agent.

The gene therapeutic agent according to the present invention can be administered to a mammal, including a human, and other animals by the HVJ liposome method (Kaneda, Experimental Medicine, Vol. 12, No. 2, 78(184), 1994; Morishita, et al., Experimental Medicine, Vol. 12, No. 15, 158(1928), 1994), a method in which the base sequence according to the present invention is administered as is by injection or the like, the calcium phosphate method, the DEAE-dextran method, the electroporation method, the gene gun method (T. M. Klein et al., Bio/Technology 10, 286–291, 1992), the lipofection method (Nabel et al., Science 244, 1285, 1990), a method using an appropriate vector (e.g., adenovirus vector, adeno-associated virus vector, herpes virus vector, vaccinia virus vector, and retrovirus vector), or the like.

In considering the local or temporary induction of apoptosis, the gene therapy agent according to the present invention is preferably administered in such a manner that ASK1 is transiently present in the body. Examples of such a manner include parenteral administration methods such as administering the base sequence according to the present invention as is by injection or the like, the lipofection method, the HVJ liposome method, a method using an adenovirus vector, and a method using a vaccinia virus vector.

Another aspect of the present invention provides a use of the protein, base sequence or vector, in particular, a use for the manufacture of a medicament.

Still another aspect of the present invention provides a method for treating malignant tumors in mammals comprising administrating the protein, base sequence or vector according to the present invention. The effective dosages, methods of administration and dosage forms can apply for this method.

Peptide and Antibody

The present invention provides a peptide consisting of the amino acid sequence 654–669 of SEQ ID NO: 1 and a peptide comprising the amino acid sequence 654–669 of SEQ ID NO: 1.

Examples of the peptide comprising the amino acid sequence 654–669 of SEQ ID NO: 1 include a peptide in which an optional amino acid sequence is added to the N-terminal and/or C-terminal of said amino acid sequence, including the protein according to the present invention.

The peptide can be used as an antigen to obtain an antibody against the protein according to the present invention. Furthermore, the protein according to the present invention is closely involved in mechanisms of apoptosis as mentioned above. Therefore, the protein according to the present invention is useful in elucidating these mechanisms of apoptosis.

The present invention provides the antibody against the peptide. The antibody in the present invention includes a polyclonal antibody and a monoclonal antibody.

The antibody according to the present invention can be produced by a method generally known by those skilled in the art. For example, the polyclonal antibody can be obtained by injecting the abovementioned peptide into an animal (e.g., a rabbit, goat, rat, mouse, and sheep) with an optional carrier (e.g., bovine serum albumin) and purifying the serum of the animal after a certain period. The monoclonal antibody can be prepared by the hybridoma fusion technique. For example, see the following literature for reference: Kohler and Milstein, Nature, 256: 495–97, 1975; Brown et al., J. Immunol., 127(2), 539–46, 1981; Brown et al., J. Biol. Chem., 255, 4980–83, 1980; Yeh et al., Proc. Natl. Acad. Sci. (USA), 76(6), 2927–31, 1976; and Yeh et al., Int. J. Cancer, 29, 269–75, 1982; Zola et al., in Monoclonal Hybridoma Antibodies: Techniques and Applications, Hurell (ed.), pp. 51–52 (CRC Press, 1982).

The peptide according to the present invention is a part of the amino acid sequence of the protein according to the present invention. Therefore, a specific reaction (i.e., immuno cross reaction) of the antibody according to the present invention can be an index for the presence of the protein according to the present invention.

Thus, another aspect of the present invention provides a protein which can be recognized by the antibody according to the present invention, and the protein according to the present invention which can be recognized by the antibody.

EXAMPLE

Example 1

Cloning of ASK1 cDNA by Polymerase Chain Reaction (PCR) Method and Determination of Amino Acid Sequence of ASK1

(1) Isolation of cDNA

A degenerate PCR-based strategy was used in an attempt to obtain a novel serine/threonine kinase cDNA according to the method described in P. ten Dijke et al., Oncogene, 8, 2879, 1993; P. Franzen et al., Cell, 75, 681, 1993, and P. ten Dijke et al., Science, 264, 101, 1994.

As a result, several human cDNA fragments encoding more distantly related protein kinases whose functions are unknown along with the recipient-type serine/threonine kinase family, were obtained.

First, a PCR fragment was obtained using a set of PCR primers derived from the conserved subdomains VII and VIII of the serine/threonine kinase family (S. Hanks et al., Science, 241, 42, 1988). Using this fragment, a corresponding nearly full-length cDNA clone was isolated (the serine/threonine kinase encoded by this cDNA is hereinafter referred to as activator of SEK1 and MKK3 (ASK1) because of its characteristics).

More specifically, an amplified oligo(dT)-primed λgt 11 cDNA library from human erythroleukemia (HEL) cells (M. Poncz et al., Blood, 69, 219, 1987) was screened with a $^{32}$P-labeled PCR fragment. Hybridization and purification of positive bacteriophage were performed as described in H. Ichijo et al., J. Biol. Chem., 268, 14505, 1993. Base sequencing was done on both strands with a Sequenase DNA sequencing kit (U.S. Biochemical Corp.). Among 18 clones obtained, the three longest clones (clones 20, 27 and 72) were entirely sequenced. The sequence of clone 72 started from the middle of the open reading frame and ended by a stretch of poly A. The sequences of clones 20 and 27 covered the 5' part of ASK1 cDNA, and the overlapping parts with clone 72 were identical in sequence. The ASK1 cDNA sequence, combining the clone 20 and clone 72, yielded a 4533-base pair sequence with an ATG codon starting at position 268 followed by a 4125-bp open reading frame encoding a protein consisting of 1375 amino acids (FIG. 1). This protein (ASK1 protein) has an estimated molecular weight of 154,715 Da.

On the other hand, another clone (clone 27) was obtained in which an open reading frame starts from the site corresponding to an amino acid at position 375 of clone 20. Because clone 27 contained a 4-bp deletion at position 805 to 808 of ASK1 cDNA, in-frame upstream stop codons were formed.

The serine/threonine kinase domain of ASK1 was found in the middle part of the ASK1 protein and had long N-terminal and C-terminal flanking sequences (FIG. 1). Furthermore, RNA blot analysis revealed a single 5-kb transcript that was expressed in various human tissues (FIG. 3). Blots with mRNAs from various human tissues (Clontech) were probed with ASK1 cDNA labeled by random priming.

(2) Homology Search by Database

A database search of ASK1 sequence outside its kinase domain showed that a short amino acid sequence in the N-terminal part contains a motif for an FK506-binding protein (FKBP)-type peptidyl-prolyl cis-trans isomerase (FIG. 1, underlined). In contrast, the kinase domain of ASK1 has evident sequence homology with members of the MAP-KKK family. The degree of homology was 30.0% with MEKK1 in mammal and 32.3% and 30.4% with SSK2 and STE11 in *Saccharomyces cerevisiae*, respectively.

Phylogenetic comparison suggested that ASK1 is distantly related to mammalian MAPKKKs (RAF-1, KSR-1, TAK-1, and TPL-2) but most closely related to the SSK2/SSK22 family of yeast MAPKKK protein, which are upstream regulator proteins of yeast HOG1 MAPK (T. Maeda et al., Science, 269, 554, 1995). (FIG. 2).

Comparison of amino acid sequences between the kinase domain of ASK1 and kinase domains of other MAPKKKs was carried out using the clustal computer alignment program of laser gene program (DNASTAR) (D. Higgins & P. Sharp, Comput. Appl. Biosci., 5, 151, 1989).

Example 2
Molecular Genetic Analysis of ASK1 Kinase Activity Using Yeast

Overall structures of ASK1 and yeast MAPKKKs, SSK2/SSK22, are different (namely, the kinase domain of SSK2 or SSK22 is located in the C-terminal part of these proteins (T. Maeda et al., Science, 269, 554, 1995)). However, it was of interest to examine whether ASK1 might act as a functional kinase in yeast and thereby complement the loss of yeast MAPKKK.

First, ASK1 cDNA was introduced into a yeast expression vector pNV11 (H. Shibuya et al., Nature, 357, 700, 1992), and whether ASK1 can restore SSK2 or SSK22 MAPKK signal deletion in a yeast mutant strain TM257-H1 (ssk2Δ, ssk22Δ, sho1Δ) ( ), which grows in a normal YPD medium but not in a hyperosmotic medium was investigated. In this connection, SHO1 is an SH3 domain-containing transmembrane osmosensor that relates to another signaling pathway leading to various hyperosmolarity responses by way of HOG1 activation independently of SSK2/SSK22. Single or double mutant strains of SHO1, SSK2 or SSK22 are resistant to hyperosmotic medium. However, it is known that if SHO1, SSK2 and SSK22 are simultaneously destroyed, the yeast cells are unable to grow in hyperosmotic medium.

Accordingly, transformants were tested for growth in the presence of 1.5 M sorbitol (FIG. 4). Specifically, five independent transformants were selected and grown on YPD plates in the presence or absence of 1.5 M sorbitol. Photographs in FIG. 4 were taken after the growth for 6 days at 30° C.

Transformants with PNV11 vector alone or ASK1 (K709R) (a mutant strain in which kinase catalytic activity was inactivated by substituting Lys 709 with Arg) vector were also tested.

Results showed that expression of ASK1, but neither vector alone nor ASK1 (K709R), complemented TM257-H1 growth in the hyperosmotic environment (FIG. 4). ASK1 could not restore the osmotic response in a PBS2 (downstream target protein of SHO1, SSK2, and SSK2 (Maeda, T. et al., Science, 269, 554, 1995))-defective yeast strain (data not shown). This observation strongly suggests that ASK1 activity observed in TM257-H1 was mediated by the PBS-HOG1 signaling pathway but not by any pathway other than the HOG1 activation.

These results, together with the fact that the mammalian counterpart of yeast HOG1 is p38 MAP kinase (J. Rouse et al., Cell, 78, 1027, 1994; J. Han et al., Science, 265, 808, 1994; J. Lee et al., Nature, 372, 739, 1994), suggested that ASK1 may be a novel mammalian MAPKKK and involved in activation of MKK3-p38 signal transduction pathway by phosphorylating MKK3.

Figure 5:
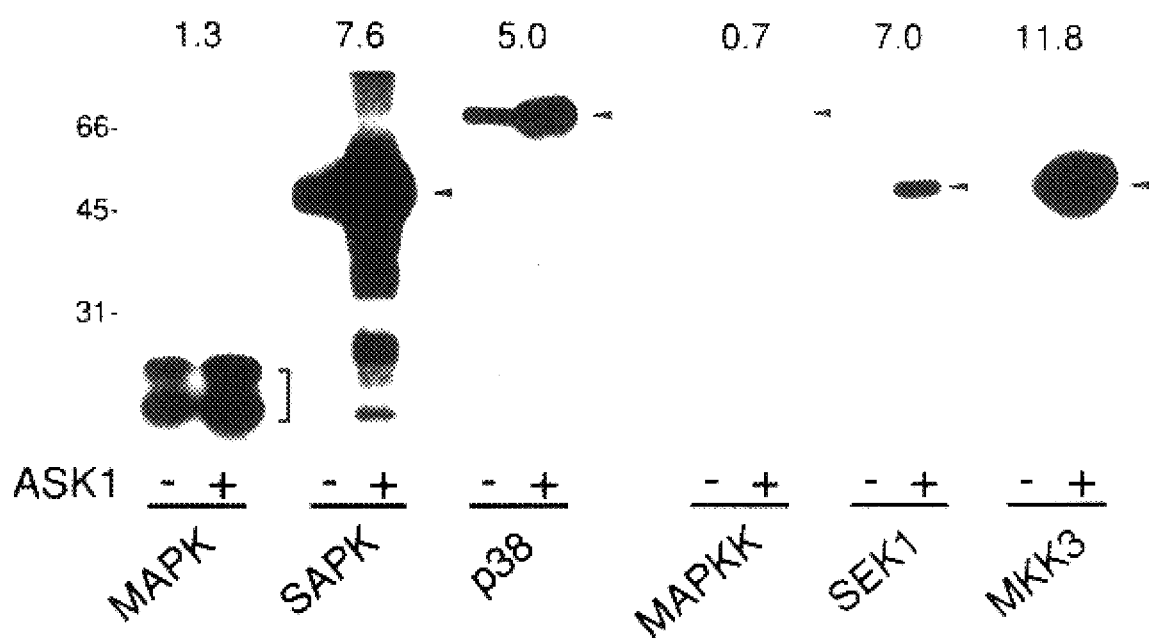
FIG. 5 is an electrophoretic photograph showing the activation of MAPKK and MAPK by ASK1 in vivo. The activation is indicated by the phosphorylation of substrate proteins. The position of each substrate protein is shown by a bracket or an arrowhead. The fold increase of kinase activity caused by coexpression of ASK1 is indicated above each lane; this figure is an average of three independent experiments. Molecular weights are indicated in kilodaltons (kDa).

Example 3
Cell Biological Analysis of ASK1 Kinase Activity Using Mammalian Cells To investigate whether ASK1 may function as an MAPKKK in mammalian cells, an ASK1 plasmid was transfected into COS7 cells together with known MAPK and MAPKK expression plasmids (FIG. 5). All the MAPK and MAPKK constructs were hemagglutinin (HA) epitope-tagged, expressed with or without ASK1, and immunoprecipitated with antibody to HA. Specifically, the following procedure was used.

The cDNAs encoding Xenopus MAPK (Y. Gotoh et al., EMBO J., 10, 2661, 1991) and Xenopus MAPKK (H. Kosako et al., EMBO J., 12, 787, 1993) were cloned as previously described. Coding regions for rat SAPKα (J. Kyriakis et al., Nature, 369, 156, 1994), human p38 (J. Han et al., Biochim. Biophys. Acta, 1265, 224, 1995), mouse SEK1 (I. Sanchez et al., Nature, 372, 794, 1994), and human MKK3 (B. Derijard et al., Science, 267, 682, 1995) were amplified by PCR method. An HA tag was introduced into the BglII-EcoRI sites of a mammalian expression vector pSRα456 (Y. Takebe et al., Mol. Cell. Biol., 8, 466, 1988), yielding pSRα-HA1. The cDNAs encoding MAPK, SAPKα, p38, MAPKK, SEK1, and MKK3 were subcloned into the BglII site of pSRα-HA1. ASK1 cDNA was introduced into another mammalian expression vector, pcDNA3 (Invitrogen). For transient expression, COS7 cells were transfected with lipofectamine (Life Technologies) according to the manufacturer's instructions. For preparing extracts, cell were lysed in a buffer solution (20 mM tris-HCl (pH 7.5), 12 mM β-glycerophosphate, 150 mM NaCl, 5 mM EGTA, 10 mM NaF, 1% Triton X-100, 0.5% deoxycholate, 3 mM dithiothreitol (DTT), 1 mM sodium vanadate, 1 mM phenylmethylsufonyl fluoride (PMSF), and aprotinin (20 μg/ml)). Cell extracts were clarified by centrifugation at 15,000 g for 10 min.

For immunoprecipitation, the supernatants were incubated with monoclonal antibody to HA (12CA5) for 1 hour at 4° C. After the addition of protein A-Sepharose (Pharmacia Biotech), the lysates were incubated for an additional 1 hour. The beads were washed twice with a solution (500 mM NaCl, 20 mM tris-HCl (pH 7.5), 5 mM EGTA, 1% Triton X-100, 2 mM DTT, and 1 mM PMSF), then twice with a solution (150 mM NaCl, 20 mM tris-HCl (pH 7.5), 5 mM EGTA, 2 mM DTT, and 1 mM PMSF), and subjected to kinase assays.

The precipitated immune complexes were subjected to a phosphorylation assay. In the assay, exogenous proteins were added as substrates. The substrate proteins used were myelin basic protein (MBP) (Sigma) for MAPK, c-Jun for SAPK, ATF-2 for p38, kinase-negative MAPK for MAPKK, and kinase-negative p38 (MPK2) for SEK1 and MKK3. ATF2 used herein was prepared according to the method previously described (S. Gupta et al., Science, 267, 389–393, 1995). Hexahistidine (His)-tagged c-Jun (S. Matsuda et al., J. Biol. Chem., 270, 12781, 1995) and glutathione-S-transferase (GST)-kinase-negative Xenopus MAPK (K57D) were prepared as described in H. Kosako et al., EMBO J., 12, 787, 1993. MPK2 (J. Rouse et al., Cell, 78, 1027, 1994), a Xenopus counterpart of mammalian p38, was used as a substrate protein for SEK1 and MKK3 in the assay.

His-tagged kinase-negative MPK2 (K54R) was prepared according to the method described in T. Moriguchi et al., J.

Biol. Chem., 270, 12969, 1995. To measure the activity to phosphorylate MBP, c-Jun, ATF2, kinase-negative MAPK, and kinase-negative MPK2, the immune complex was incubated for 30 minutes at 30° C. with 3 μg of each substrate protein in a final volume of 25 μl of a solution (20 mM Tris-HCl (pH 7.5), 10 mM $MgCl_2$, 100 μM [γ-$^{32}$P]ATP (0.3 μCi)). The reaction was stopped by addition of Laemmli's sample buffer and boiling. After SDS-polyacrylamide gel electrophoresis (PAGE), phosphorylation of these proteins was quantified with an image analyzer (FujiX BAS2000).

Results showed that ASK1 expression induced 7.6- and 5.0-fold activation of SAPK and p38 MAP kinase, respectively, but only weakly activated MAPK (FIG. 5).

Furthermore, ASK1 activated MKK3 and SEK1 up to 11.8- and 7.0-fold, respectively. In contrast, no detectable activation of MAPKK was observed (FIG. 5).

Example 4
In Vitro-coupled Kinase Assay with Recombinant Proteins

To investigate whether the MKK3 activation observed in FIG. 5 was a direct effect by ASK1, an in vitro-coupled kinase assay with recombinant SEK1, MKK3, MAPKK6, and recombinant kinase-negative p38 (MPK2) proteins was used. In this Example, ASK1 expressed in COS7 cells was immunoprecipitated with polyclonal antibody as described in Example 3, and the resulting immune complex was used as an ASK1 enzyme standard. The anti-ASK1 polyclonal serum used in the immunoprecipitation was raised against the peptide sequence (SEQ ID NO:3) (TEEKGRSTEEGDCESD), corresponding to amino acids 654 to 669 of ASK1, that was coupled to keyhole limpet hemocyanin by a glutaraldehyde method, mixed with Freund's adjuvant, and used to immunize rabbits according to the method described in H. Ichijo et al., J. Biol. Chem., 270, 7420, 1995. The coupled kinase assay was carried out using recombinant SEK1, MKK3, MAPKK6, and recombinant kinase-negative p38 proteins together with this immune complex according to the following procedure.

His-tagged Xenopus MAPKK and human MKK3 were expressed in Escherichia coli and purified as described in Y. Gotoh et al., Oncogene, 9, 1891, 1994. To measure the activity of an immune complex to activate MAPKK or MKK3, 0.2 μg of His-MAPKK or His-MKK3 was first incubated with the immune complex for 15 minutes at 30° C. in a final volume of 25 μl of a solution (20 mM Tris-HCl (pH 7.5), 10 mM $MgCl_2$, and 100 μM ATP). Subsequently, 0.3 μCi of [γ32P] ATP and 3 μg of GST-kinase-negative MAPK (to MAPKK) or His-kinase-negative MPK2 (to MKK3) were incubated in the same buffer solution (final volume, 35 μl) for 7 minutes at 25° C. Samples were then analyzed by SDS-PAGE and image analyzer. Results are shown in FIG. 6.

ASK1 immunoprecipitates from COS7 cells strongly activated SEK1, MKK3, and MAPKK6 activity (greater than 40-fold for each), and phosphorylation of p38 was observed only when ASK1 was present in the kinase assay. ASK1-dependent phosphorylation of p38 was further confirmed to result in the activation of p38 using wild-type p38 and ATF2. In contrast, ASK1 weakly activated MAPKK (2.2-fold) even in the presence of MAPKK.

When Raf was used as MAPKKK for a positive control, a 27.8-fold activation of MAPKK was observed (date not shown). These results (Example 4) and the results in Example 3 indicated that ASK1 is a novel MAPKKK, which selectively activates the SEK1-SAPK and MKK3/MAPKK6-p38 pathways.

Example 5
Induction of Apoptosis by ASK1 Expression
(1) Confirmation of ASK Expression The biological activity of ASK1 was investigated using mink lung epithelial (Mv1Lu) cell lines that were stably transfected with metallothionein promoter-based expression plasmids. To avoid the possibility that constitutively expressed ASK1 might induce cell death, resulting in a failure to obtain stable transformants, a metallothionein-inducible promoter system was used.

ASK1 and ASK1(K709R) cDNA were subcloned into pMEP4 vector (Invitrogen) at convenient enzyme cleavage sites. Transfection of cDNAs was done with Transfectam (Promega) according to the manufacturer's instructions. Selection by hygromycin B was done by the method described in M. Saitoh et al., J. Biol. Chem., 271, 2769, 1996. Several independent clones were ring-cloned, and the expression of ASK1 protein was determined by immunoprecipitation (H. Ichijo et al., J. Biol. Chem., 268, 14505, 1993) with antiserum to ASK1. Two independent positive clones were used for the assays with essentially the same results.

Cells were metabolically labeled with a mixture of [$^{35}$S] methionine and [$^{35}$S]cysteine in the presence or absence of 100 μM $ZnCl_2$ for 5 hours. The cellular lysates were then subjected to immunoprecipitation with antiserum to ASK1, SDS-PAGE, and fluorography.

Figure 7:
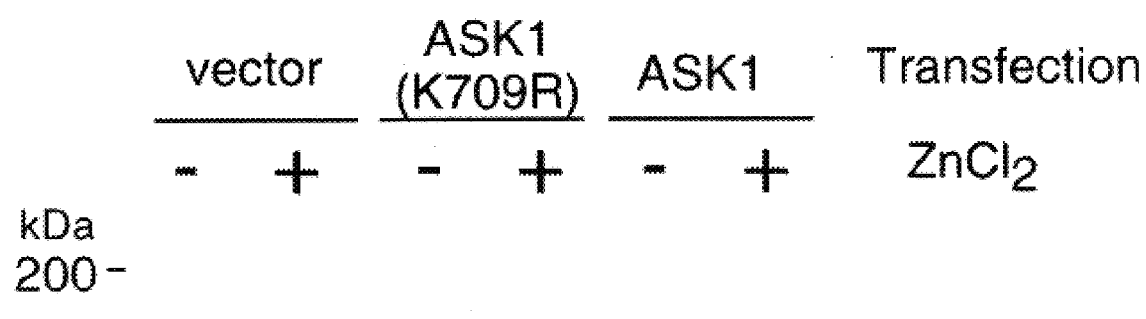
FIG. 7 is an electrophoretic photograph showing $ZnCl_2$-dependent expression of ASK1 and ASK1(K709R) in stably transfected Mv1Lu cells (transfection).

Results are shown in FIG. 7. It was revealed that ASK was highly expressed only when induced by ZnCl2. ASK1 (K709R)-transfected cells expressed the recombinant protein in similar amounts.

(2) Effects on Thymidine Incorporation

To investigate the effects of ASK1 on cellular growth, Mv1Lu cells stably transfected with vector alone (FIG. 8, black squires), ASK1 (FIG. 8, black circles), and ASK1 (K709R) (FIG. 8, white circles) were incubated in MEM containing 1% fetal bovine serum (FBS) and the indicated concentration of $ZnCl_2$ for 16 hours. The cells were then pulse-labeled with [$^3$H]thymidine for 1 hour, and [$^3$H] radioactivity incorporation into the DNA was determined using a liquid scintillation counter. Results are shown in FIG. 8.

Drastic inhibition of [$^3$H]thymidine incorporation was observed in the cells transfected with ASK1. In contrast, no inhibition was observed in the cells transfected with the vector alone or ASK1(K709R) vector (FIG. 8). Correlation between dose-dependent inhibition of [$^3$H]thymidine incorporation by $ZnCl_2$ and the dose-dependent expression and activation of ASK1 was investigated. The ASK1-transfected Mv1Lu cells were treated with the indicated amount of $ZnCl_2$ for 5 hours, and then the level of ASK1 was determined by immunoprecipitation (FIG. 9, top). Furthermore, the cells were treated with the indicated amount of $ZnCl_2$ for 5 hours, ASK1 was recovered from the cells by immunoprecipitation and then subjected to the MKK3-MPK2 coupled kinase assay (FIG. 9, bottom). Results showed that the dose-dependent inhibition of [$^3$H]thymidine incorporation by $ZnCl_2$ correlated well with the dose-dependent expression and activation of ASK1 (FIG. 9).

(3) Effects on Enhancement of SAPK and p38 Kinase Activity

The following experiment was carried out to investigate correlation between ASK1 activity and endogenous SAPK and p38 activation.

Figure 10:
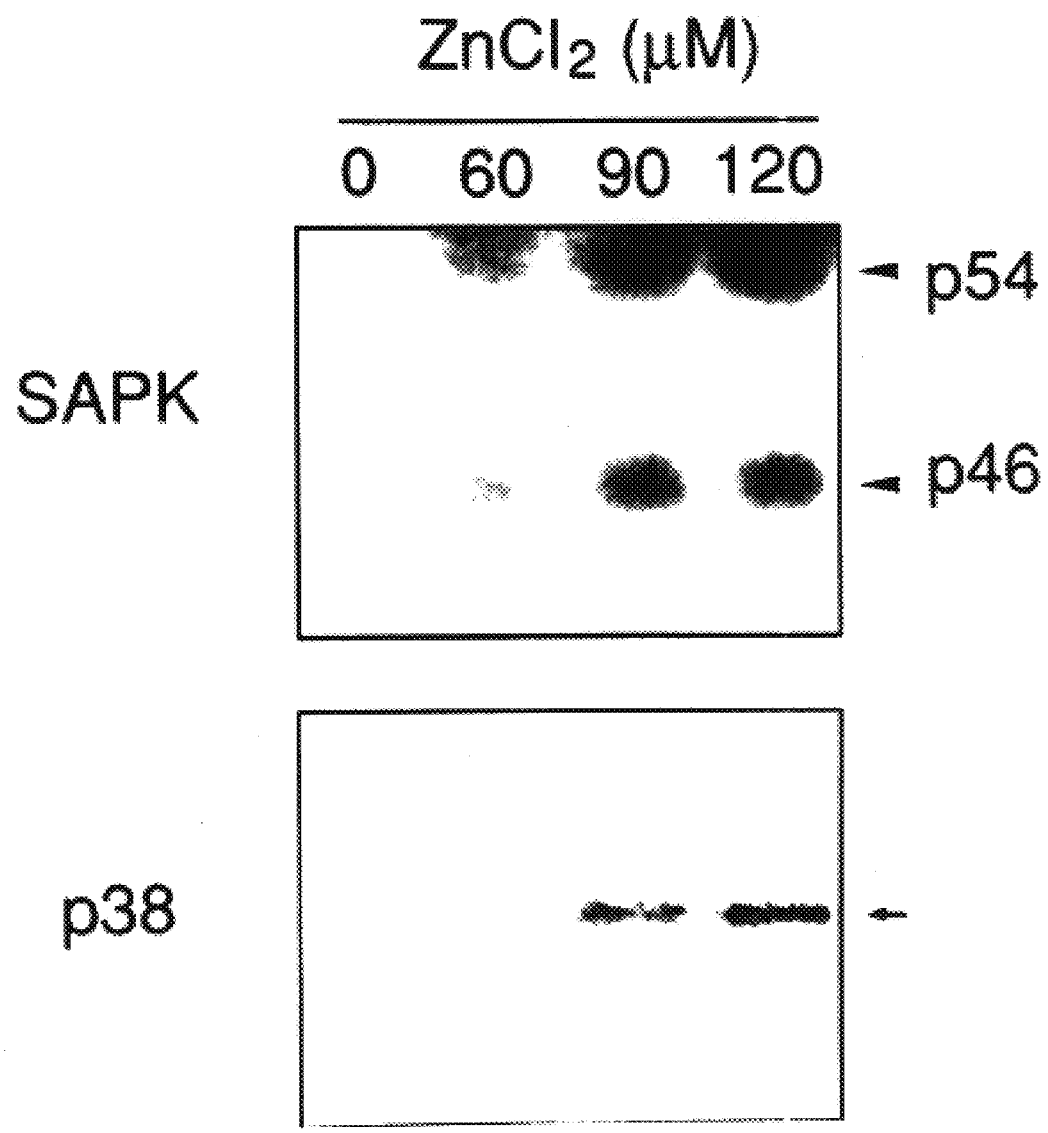
FIG. 10 is an electrophoretic photograph showing ASK1-dependent activation of endogenous SAPK (top) and p38 (bottom). The positions of p54 and p46 SAPK (top) and ATF2 (bottom) are indicated by arrowheads and an arrow, respectively.

Mv1Lu cells stably transfected with ASK1 were incubated with the indicated concentration of $ZnCl_2$ for 5 hours. To measure the activity of SAPK, each cell extract was subjected to a kinase detection assay (in-gel kinase assay) within a polyacrylamide gel containing c-Jun as a substrate protein according to the method described in S. Matsuda et al., J. Biol. Chem., 270, 12781, 1995. To examine the activity of p38, p38 was immunoprecipitated with polyclonal antibody to p38 (C-20, Santa Cruz) according to the method described in Example 3 except for the presence of 0.1% SDS during the immunoprecipitation. The kinase activity was then detected using ATF2 as a substrate protein. Results are shown in FIG. 10.

It was revealed that endogenous SAPK and p38 were also activated in parallel with the ASK1 activities. (4) Effects on cell morphology and DNA fragmentation It was revealed that morphological changes (namely, cytoplasmic shrinkage and cellular condensation) were induced within 6 hours after addition of $ZnCl_2$ when cells were treated with 100 $\mu M$ $ZnCl_2$ and ASK1 was continuously expressed (data not shown). These morphological changes were not observed in the cells in which ASK1 (K709R) was expressed. Cells were incubated with MEM containing 1% FBS in the presence or absence of 100 $\mu M$ $ZnCl_2$ for 26 hours. The typical morphological properties of apoptotic cells, i.e., cytoplasmic shrinkage and cellular condensation, became most evident after induction for long hours (26 hours) (FIG. 11, top).

Figure 12:
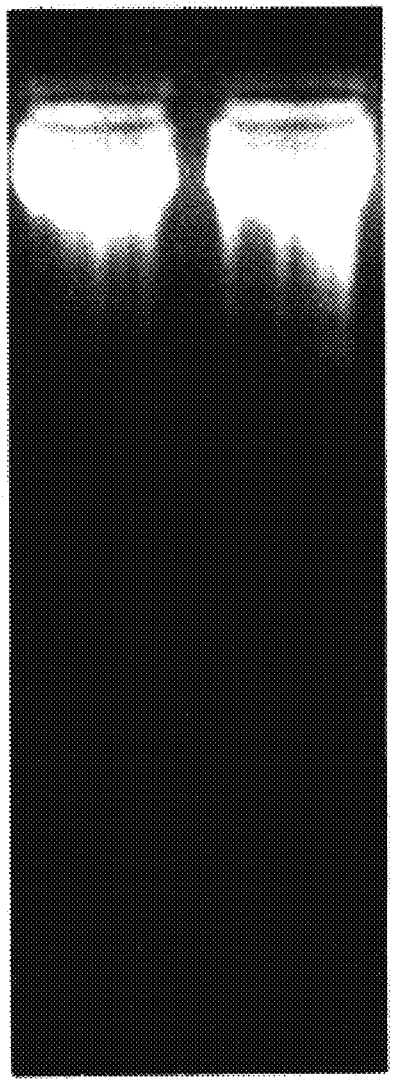
FIG. 12 is an electrophoretic photograph showing ASK1-dependent DNA fragmentation.

Whether ASK1 induces the apoptotic cell death was investigated by an in situ staining of cells with the terminal deoxynucleotidyl transferase-mediated dUTP nick end labeling (TUNEL) method (FIG. 11, bottom) as well as by genomic DNA fragmentation. More specifically, Mv1Lu cells transfected with ASK1 were incubated with MEM without FBS in the presence or absence of 100 $\mu M$ $ZnCl_2$ for 25 hours and then stained by TUNEL method with a situ cell death detection kit (Boehringer Mannheim) (FIG. 11, bottom), or the total DNA was isolated and subjected to 2% agarose gel electrophoresis (FIG. 12). As a result, apoptosis and DNA fragmentation were observed after induction of ASK1 expression by $ZnCl_2$ (FIG. 11, bottom, and FIG. 12).

Example 6

ASK1 Activation by TNF-α

In this Example, whether the treatment of cells with TNF-α resulted in the activation of ASK1 was examined. Mv1Lu cells transfected with ASK1 were first treated with 50 $\mu M$ $ZnCl_2$ for 5 hours to induce ASK1 expression. The cells were then stimulated with TNF-α (100 ng/ml) for the indicated time. ASK1 immunoprecipitates derived from TNF-α-treated cells were subjected to a coupled kinase assay with MKK3 and kinase-negative p38 (FIG. 13, top and bottom, and FIG. 14).

Figure 13:
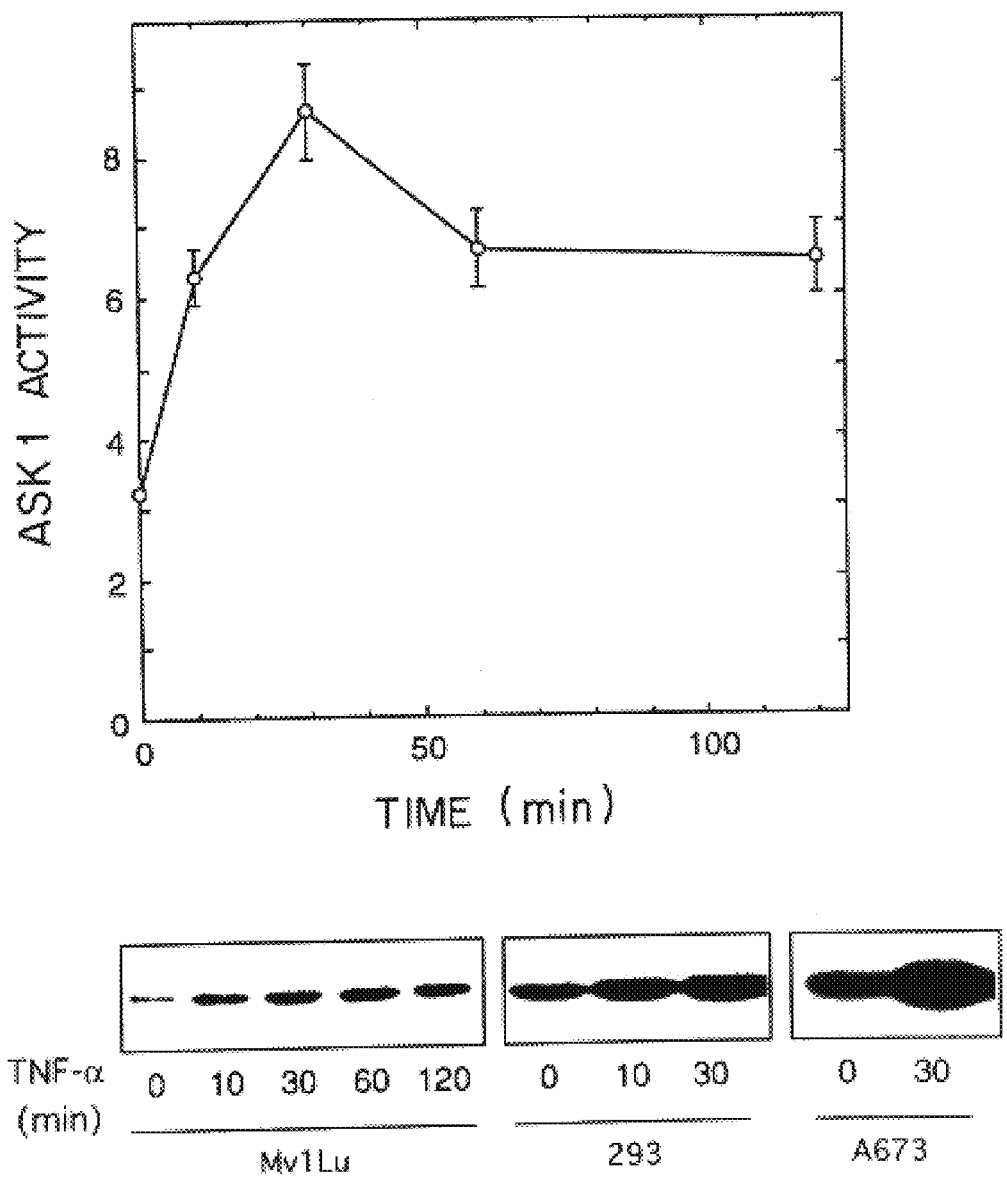
FIG. 13 shows activation, with time, of ASK1 by TNF-α in various cells. (Top) Values of ASK1 activity in Mv1Lu cells transfected with ASK1 are given as relative values. The results are mean values from at least five independent experiments. Error bars indicate the standard deviations. (Bottom) The figure shows ASK1 activity, with time (minutes), in ASK1-transfected Mv1Lu cells and non-ASK1 transfected 293 cells and A673 cells treated with TNF-α.

The results showed that the treatment of cells with TNF-α activated the ASK1 in ASK1-transfected Mv1Lu cells within 5 minutes (FIG. 13, top and bottom). The ASK1 was activated by TNF-α in a dose-dependent manner (FIG. 14).

ASK1-nontransfected 293 cells and A673 cells were treated with TNF-α (100 ng/ml). The results showed that endogenous ASK1 was also activated by TNF-α in other various cell types in which apoptosis is induced by TNF-α (data not shown), including human 293 embryonal kidney cells, A673 rhabdomyosarcoma cells (FIG. 13, bottom), Jurkat T cells, and KB epidermal carcinoma cells (data not shown).

Figure 16:
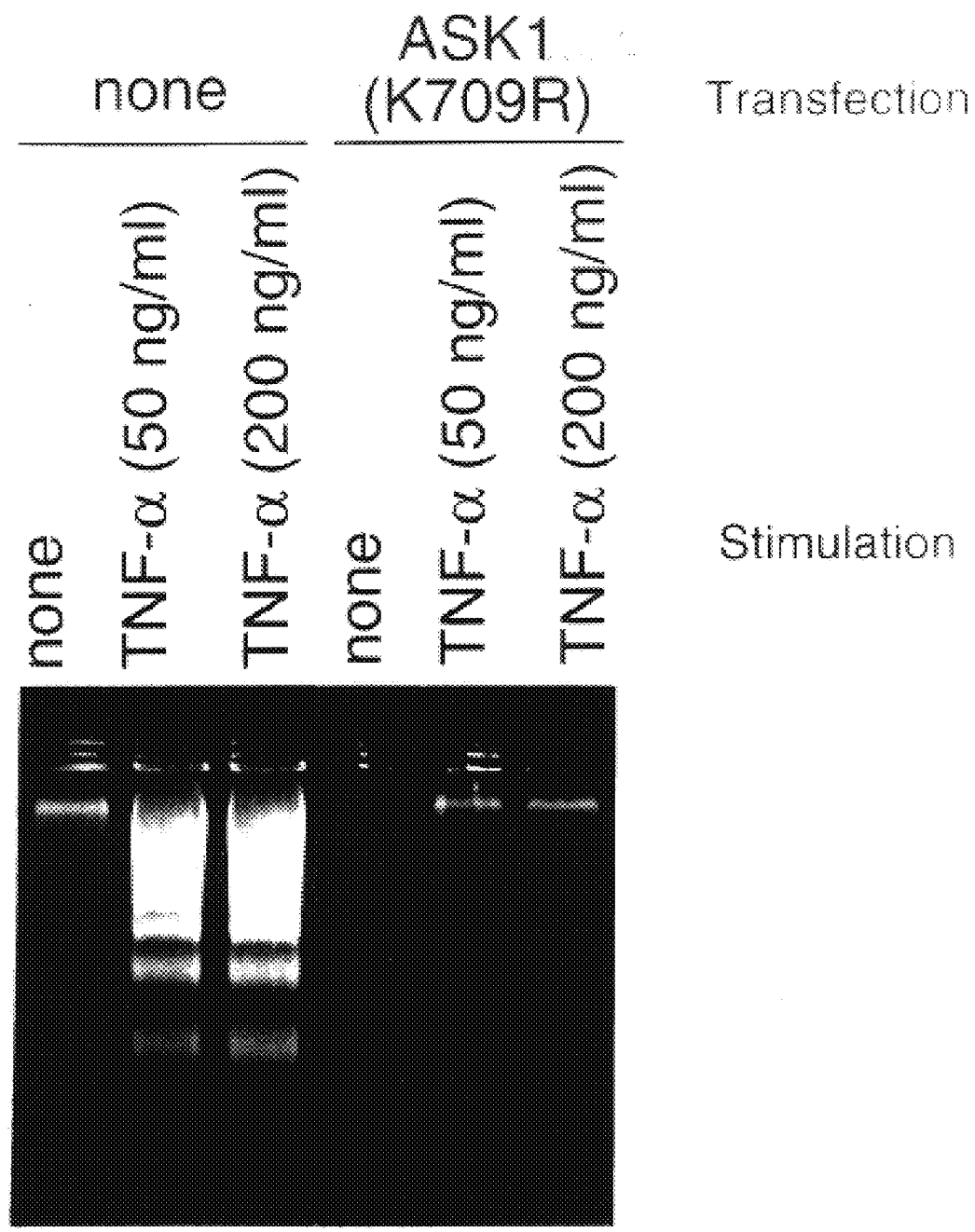
FIG. 16 is an electrophoretic photograph showing that DNA fragmentation in Jurkat T cells stimulated by TNF-α in the presence or absence (none) of actinomycin D is inhibited by transfection with ASK1(K709R). In the Figure, "none" represents the case where cells are not transfected or not stimulated.

Furthermore, ASK1(K709R) was transiently transfected into 293 cells (FIG. 15) or Jurkat T cells (FIG. 16). Specifically, the experiment was carried out according to the following method. 293 cells ($2\times10^6$) were transiently transfected with 2 $\mu g$ of pcDNA3 control vector or pcDNA3-ASK1(K709R) by the use of Tfx-50 (Promega) according to the manufacturer's protocol. Eight hours after transfection, cells were treated with TNF-α (100 ng/ml) with or without 300 nM actinomycin D (ActD) for 16 hours. Apoptotic cells detached from culture plate were collected, and total DNA was isolated and analyzed by 2% agarose gel electrophoresis (FIG. 15).

Furthermore, the pcDNA3-ASK1 (K709R) was transfected into Jurkat cells by DMRIE-C reagent (Life Technologies) together with pHook-1 plasmid (Invitrogen). Further, the pHook-1 plasmid encodes a single-chain antibody fusion protein directed to the hapten phox (4-ethoxymethylene-2-phenyl-2-oxazolin-5-one). Therefore, it is possible to selectively isolate transfected cells with magnetic beads coated with phOx.

ASK1(K709R)-transfected populations of cells (cotransfection efficiency was nearly 100% as determined by β-galactosidase staining) were isolated on phOx-coated magnetic beads with the Capture-Tec kit (Invitrogen), after which the cells were incubated with various concentrations of TNF-α for 5.5 hours. Cytoplasmic small fragmented DNA was isolated as described (Selins, K. & Cohen, J., J. Immunol., 139, 3199, 1987) with minor modifications. Cells ($3\times10^6$) were lysed with 200 $\mu l$ of a buffer solution (20 mM Tris-HCl (pH 7.5), 10 mM EDTA, 0.5% Triton X-100). The resulting lysate was incubated with proteinase K (0.2 mg/ml) and RNase N (0.1 mg/ml) at 42° C. for 1 hour. DNA was then purified by phenol-chloroform extraction after ethanol extraction. The extracted cytoplasmic DNA was analyzed by 2% agarose gel electrophoresis (FIG. 16).

The results showed that DNA fragmentation induced by TNF-α was effectively reduced. Further, nontransfected Jurkat cells and isolated Jurkat cells (that were transfected with pHook-1 and control pcDNA3 plasmid) were similarly sensitive to TNF-α in the DNA fragmentation assay (date not shown). This observation suggested that ASK1(K709R) acts as a dominant-negative mutant, and more importantly, that ASK1 is essential for the TNF-α-induced apoptotic response.

What is claimed is:

1. An isolated protein comprising the amino acid sequence of SEQ ID NO: 1.

2. An isolated protein comprising the amino acid sequence of SEQ ID NO: 1 that has one addition, one insertion, one substitution, and/or one deletion and that enhances SEK1 kinase activity and/or MKK3 kinase activity.

3. An isolated protein consisting essentially of the amino acid sequence of SEQ ID NO: 1.

4. An isolated protein comprising the amino acid sequence of SEQ ID NO: 1 which has one addition, one insertion, one substitution, and/or one deletion and lacks protein kinase activity.

5. An isolated protein as claimed in claim 4 having substitution K709R.

6. An isolated nucleotide sequence encoding a protein according to claim 1.

7. An isolated nucleotide sequence according to claim 6, which comprises the DNA sequence of SEQ ID NO: 2.

8. An isolated nucleotide sequence encoding a protein of claim 4.

9. A vector comprising a nucleotide sequence of claim 6.

10. A vector comprising a nucleotide sequence of claim 8.

11. A vector as claimed in claim 9, selected from the group consisting of plasmid vectors, virus vectors and liposome vectors.

12. A host cell transformed with a vector of claim 9.

13. A host cell as claimed in claim 12 selected from the group consisting of *Escherichia coli,* yeast cells, insect cells, COS cells, mink pulmonary epithelial cells, lymphocytes, fibroblasts, NIH/3T3 cells, CHO cells, blood cells and tumor cells.

14. A method for producing a protein that has protein kinase activity and enhances SEK1 kinase activity and/or MKK3 kinase activity, which comprises culturing host cells of claim 12 and isolating said protein from the culture product.

15. An agent comprising a protein according to claim 1 and a pharmaceutically acceptable carrier.

16. A gene therapeutic agent for use in the treatment of malignant tumors, comprising (A) a vector of claim 9 and (B) a pharmaceutically acceptable carrier.

17. A peptide consisting of the amino acid sequence of 654–669 of SEQ ID NO: 1.

18. An isolated protein comprising the amino acid sequence 678 to 936 of SEQ ID NO:1, wherein said isolated protein has SEK1 kinase activity and/or MKK3 kinase activity.

19. An isolated nucleotide sequence encoding a protein according to claim 2.

20. An isolated nucleotide sequence encoding a protein according to claim 5.

21. An isolated nucleotide sequence encoding a protein according to claim 18.

22. An agent comprising a protein according to claim 2 and a pharmaceutically acceptable carrier.

23. An agent comprising a vector comprising the nucleotide sequence of claim 19 and a pharmaceutically acceptable carrier.

24. An agent comprising a nucleotide sequence of claim 6 and a pharmaceutically acceptable carrier.

25. An agent comprising a nucleotide sequence of claim 19 and a pharmaceutically acceptable carrier.

* * * * *

Disclaimer

6,194,187 B1 — Kohei Miyazono, Shiki (JP); Hidenori Ichijo, Bunkyo-ku (JP). APOPTOSIS-INDUCING PROTEIN AND GENE ENCODING THE SAME. Patent dated February 27, 2001. Disclaimer filed October 11, 2011, by the assignee, Japanese Foundation for Cancer Research.

Hereby disclaims the entire term of all claims 1-25 of said patent.

*(Official Gazette, August 18, 2015)*